US007846692B2

(12) United States Patent
Cheek et al.

(10) Patent No.: US 7,846,692 B2
(45) Date of Patent: Dec. 7, 2010

(54) HE4 MONOCLONAL ANTIBODIES AND METHODS FOR THEIR USE

(75) Inventors: Robert L. Cheek, Mebane, NC (US); Timothy J. Fischer, Raleigh, NC (US); John W. Groelke, Raleigh, NC (US)

(73) Assignee: Tripath Imaging, Inc., Burlington, NC (US)

( * ) Notice: Subject to any disclaimer, the term of this patent is extended or adjusted under 35 U.S.C. 154(b) by 27 days.

(21) Appl. No.: 12/044,302

(22) Filed: Mar. 7, 2008

(65) Prior Publication Data
US 2008/0254048 A1 Oct. 16, 2008

Related U.S. Application Data

(60) Provisional application No. 60/906,126, filed on Mar. 9, 2007.

(51) Int. Cl.
*C12P 21/04* (2006.01)
(52) U.S. Cl. ............... 435/70.21; 424/184.1; 530/387.1
(58) Field of Classification Search ............. 435/70.21; 424/184.1; 530/387.1
See application file for complete search history.

(56) References Cited

U.S. PATENT DOCUMENTS 7,270,960 B2 9/2007 Hellstrom et al.
2002/0182619 A1 12/2002 Lillie et al.

FOREIGN PATENT DOCUMENTS

WO WO 01/16354 A1 3/2001
WO WO 03/021273 3/2003
WO WO 2006/089125 A2 8/2006

OTHER PUBLICATIONS

Bendayan et al, 1995, J Histochem Cytochem, 43(9): 881-886.*
Bowie (Science, 1990, 257:1306-1310).*
Schmid S et al, 2001 (J comparative Neurology, 430(2): 160-71).*
Conner et al, 1996 (Mol Brain Res, 42: 1-17).*
Stanton, P et al, 1994, Br J Cancer, 70: 427-433.*
Iehle, C et al, 1999, J Steroid Biochem Mol Biol, 68: 189-195.*
Abbaszadegan, M R, et al, 1994, Cancer Res, 54: 4676-4679.*
Tockman et al (Cancer Res., 1992, 52:2711s-2718s).*
Glinsky et al, 2004, J Clin Invest, 113: 913-923.*
Bost et al, 1988, Immunol Investigation, 17 (6&7): 577-586).*
Banki et al, 1994, JBC, 269 (4): 2847-51.*
Bingle, L. et al., "The Putative Ovarian Tumour Marker Gene HE4 (WFDC2), is Expressed in Normal Tissues and Undergoes Complex alternative Splicing to Yield Multiple Protein Isoforms," *Oncogenes*, 2002, pp. 2768-2773, vol. 21.
Cheek, R., et al., "The Molecular Characterization of two Novel Antibodies to HE4 and Their Untility in Detecting Early Stage Ovarian Cancer," *Proceedings of the American Associtaion for Cancer Research*, 2007, pp. 636, vol. 48.

Hellström, I., et al., "The HE4 (WFDC2) Protein is a Biomarker for Ovarian Carcinoma," *Cancer Research*, 2003, pp. 3695-3700, vol. 63.
Scholler, N., et al., "Method for Generation of in vivo Biotinylated Recombinant Antibodies by Yeast Mating," *Journal of Immunological Methods*, 2006, pp. 132-143, vol. 317.
Scholler, N., et al., "Bead-Based ELISA for Validation of Ovarian Cancer Early Detection Markers," *Clin. Cancer Res.*, 2006, pp. 2117-2124, vol. 12(7).
Drapkin, R., et al.., "Human Epididymis Protein 4 (HE4) Is a Secreted Glycoprotein That Is Overexpressed by Serous and Endometrioid Ovarian Carcinomas," *Cancer Res.*, 2005, pp. 2162-2169, vol. 65(6).
Kirchhoff, C., et al., "A Major Human Epididymis-Specific cDNA Encodes a Protein With Sequence Homology to Extracellular Proteinase Inhibitors," *Biology of Reproduction*, 1991, pp. 350-357, vol. 45.
Kirchhoff, C., "Molecular Characterization of Epididymal Proteins," *Reviews of Reproduction*, 1998, pp. 86-95, vol. 3.
Wang, K., et al., "Monitoring Gene Expression Profile Changes in Ovarian Carcinomas Using cDNA Microarray," *Gene*, 1999, pp. 101-108, vol. 229.
Welsh, J.B., et al., "Analysis of Gene Expression Profiles in Normal and Neoplastic Ovarian Tissue Samples Identifies Candidate Molecular Markers of Epithelial Ovarian Cancer," *PNAS*, Jan. 2001, pp. 1176-1181, vol. 98(3).
Nilsson, O., et al., "HE4--A New Marker in Ovarian and Endometrial Cancer," XI International Symposium on Biology and Clinical Usefulness of Tumor Markers, Barcelona, Feb. 22, 2007.

* cited by examiner

*Primary Examiner*—Larry R. Helms
*Assistant Examiner*—Minh-Tam Davis
(74) *Attorney, Agent, or Firm*—Alston & Bird LLP

(57) ABSTRACT

Compositions and methods for diagnosing ovarian cancer in a patient and for identifying patients with an increased likelihood of having ovarian cancer are provided. The compositions include novel monoclonal antibodies, and variants and fragments thereof, that specifically bind to HE4. Monoclonal antibodies having the binding characteristics of an HE4 antibody of the invention are further provided. Hybridoma cell lines that produce an HE4 monoclonal antibody of the invention are also disclosed herein. The compositions find use in diagnostic methods as well as in screening methods for identifying patients having an increased likelihood of having ovarian cancer. Kits comprising one or more of the disclosed HE4 monoclonal antibodies and for practicing the methods of the invention are further provided. Polypeptides comprising the amino acid sequence for an HE4 epitope and methods of using these polypeptides in the production of antibodies are also encompassed by the present invention.

11 Claims, 2 Drawing Sheets

HE4 MONOCLONAL ANTIBODIES AND METHODS FOR THEIR USE

CROSS REFERENCE TO RELATED APPLICATIONS

This application claims the benefit of U.S. Provisional Application Ser. No. 60/906,126, filed Mar. 9, 2007, which is incorporated herein by reference in its entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 339943SequenceListing.txt, a creation date of Mar. 7, 2008, and a size of 14.7 KB. The sequence listing filed via EFS-Web is part of the specification and is hereby incorporated in its entirety by reference herein.

FIELD OF THE INVENTION

The invention relates to antibodies capable of binding to human epididymis protein 4 (HE4) and methods of using these antibodies, particularly in methods for diagnosing ovarian cancer and for identifying patients with an increased likelihood of having ovarian cancer.

BACKGROUND OF THE INVENTION

Ovarian cancer represents a heterogeneous group of diseases that affect women on a global basis. There are several forms of ovarian cancer which include epithelial cancer, germ-line cancer of the ovaries and ovarian stromal cancer. Epithelial ovarian cancer represents the most common form of the disease. Approximately 5-10% of epithelial ovarian cancer represents a hereditary form of the disease and three common patterns are recognized: ovarian cancer alone; ovarian and breast cancer linked to BRAC1 and BRCA2 genetic linkage on chromosomes 17q21 and 13q12 respectively; and ovarian and colon cancer. The most important risk factor for ovarian cancer is a first degree relative with the disease (e.g., a mother, sister or daughter with ovarian cancer). See, for example, Patridge et al. (1999) *CA-A Cancer Journal for Clinicians* 49:297-320. In 2005, there were an estimated 22,000 new cases of ovarian cancer diagnoses and 16,000 deaths from ovarian cancer. See generally American Cancer Society website at www.cancer.org; National Cancer Institute website at www.cancer.gov. Ovarian cancer is a disease that primarily affects post-menopausal women with the median age for diagnosis at 63 years of age. However, the disease can affect women at all age groups. National Cancer Institute Surveillance, Epidemiology, and End Results (SEER) Program at www.seer.cancer.gov.

The classification of ovarian cancer stage is based upon the extent of localization versus spread of the disease beyond the ovaries. Stage 1 ovarian cancer is confined to one or both of the ovaries. Stage 2 disease involves a tumor in one or both ovaries with pelvic extension. In Stage 3 ovarian cancer, a tumor is present in or both ovaries with microscopically confirmed peritoneal metastasis outside the pelvis and/or regional lymph node metastasis. Stage 4 ovarian cancer is characterized by distant metastasis beyond the peritoneal cavity. Ovarian cancer is generally diagnosed in an advance stage of the disease due to the lack of specific clinical symptoms that would indicate the presence of small tumors. For women under the age of 50, less than 40% of ovarian cancers are detected when tumors are localized to one or both ovaries and when disease prognosis is best. For women over the age of 50, that number drops to less than 15%. Approximately 68% of women of all age groups afflicted with ovarian cancer are not diagnosed until distant metastasis is present. See generally National Cancer Institute Surveillance, Epidemiology, and End Results (SEER) Program at www.seer.cancer.gov.

Ovarian cancer spreads via local shedding from the ovarian epithelium into the peritoneal cavity followed by implantation on the peritoneum and local invasion of the bowel and bladder. The presence of lymph node involvement in ovarian cancer is evident in all stages of diagnosed ovarian cancer. The percentage of positive lymph nodes increases significantly with progression of the disease (i.e., Stage 1, 24%; Stage 2, 50%, Stage 3, 74%; Stage 4, 73%). Id.

The survival of patients with ovarian cancer is a function of the stage at which the disease is diagnosed, with the 5-year survival decreasing with advanced disease. More than 90% of women diagnosed with ovarian cancer in Stage 1 survive for at least 5 years following diagnosis. The 5-year survival rate drops to less than 30% when the disease is not diagnosed until Stage 4 (i.e., distant metastasis). Id.

Epithelial ovarian cancer is the most common form of the disease. There are four recognized major histological classes of epithelial ovarian cancer and include serous, endometrioid, clear cell, and mucinous subtypes. The pathogenesis of ovarian cancer is poorly understood but is believed to arise from ovarian surface epithelium. See Bell (2005) *Mod. Pathol.* 18 (Suppl 2):S19-32. Life factors that provide the greatest reduction in risk of ovarian cancer include multiparity, use of oral contraceptives, and breast feeding, all of which prevent ovulation. Because ovulation results in epithelial damage, followed by repair and possible inflammatory responses, repetition of this process throughout a woman's reproductive life without interruption appears to lead to cell damage and to increase the risk of ovarian cancer. See, for example, Ness et al. (1999) *J. Natl. Cancer Inst.* 91:1459-1467. However, there is no recognized, stepwise progression of ovarian cancer through defined precursor lesions, such as those recognized for both cervical carcinoma and colon cancer. Hence, considerable research has been directed at understanding the molecular basis for ovarian cancer and to understand the basic differences between the various histological subtypes of ovarian cancer. These studies have utilized gene expression analysis to provide this understanding and have identified a series of potential biomarkers for evaluation in diagnostic applications. See for example Ono et al. (2000) *Cancer Res.* 60:5007-11; Welsh et al. (2001) *Proc. Natl. Acad. Sci. USA* 98:1176-1181; Donninger et al. (2004) *Oncogene* 23:8065-8077; and Lee et al. (2004) *Int. J. Oncol.* 24(4):847-851.

Ovarian cancer is often detected with the presentation of overt clinical symptoms, most notably the presentation of abdominal pain, an adnexal mass, abdominal bloating, and urinary urgency. As such, the detection of ovarian cancer is often detected at an advanced stage, where the prognosis and clinical outcome is poor. Detection of ovarian cancer at an early stage (i.e., Stage 1) results in approximately 90% cure rate using standard surgery and chemotherapy; hence there is a clinical need to detect ovarian cancer at an early stage where treatment will be most effective. Unfortunately, current screening methods to detect early stage ovarian cancer are insufficient. The current practice for ovarian cancer screening employs the use of CA125 and transvaginal ultrasound (sonography). Rising serum levels of CA125 are associated with ovarian cancer and subsequent utilization of transvaginal ultrasound helps detect the presence of ovarian cancer. Confirmation of ovarian disease is based upon invasive procedures such as laparotomy. However, the use of CA125 is ineffective for general population screening due to issues of limited sensitivity, limited specificity, and a poor positive predictive value of <3%. Bast (2003) *J Clin Oncol.* 21(10 Suppl):200-205. As a result, there is no consensus on the recommendations for generally screening for ovarian cancer in the asymptomatic patient population. See National Cancer Institute Web Site at www.cancer.gov. For high risk patients, the generally accepted procedures for the detection of ovarian cancer include the use of pelvic examinations, the use of CA125 serum testing, and transvaginal ultrasound (sonography). Patridge et al. (1999) *CA-A Cancer Journal for Clinicians* 49:297-320.

CA125 is a well characterized tumor marker normally expressed on the surface of epithelial cells and is often detected in the serum of normal patients at 35 U/mL. Elevated serum levels of CA125 (>35 U/mL) are often detected in approximately 85% of ovarian cancer patients; the remaining 15% of ovarian cancer patients have normal serum levels of CA125. Furthermore, CA125 is elevated in only 50% of stage 1 ovarian cancer patients, thereby limiting its clinical utility in the early detection of ovarian cancer. However, elevated serum levels of CA125 are used for the monitoring of disease recurrence following therapeutic intervention and this represents the currently approved use for CA125 by the FDA. In addition, elevated serum levels of CA125 are predictive of future detectable ovarian cancer.

The low prevalence rates of ovarian cancer in the general population create significant challenges for the development of a screening test that would promote early detection of the disease. Screening methods for diseases with low prevalence rates such as ovarian cancer often result in a high ratio of false positives to true positives, which limits the clinical utility of such screening programs. Given the significant risks associated with surgical exploration for possible ovarian cancer, a clinically useful screening test should refer to surgery no more than 10 women for every woman who actually has ovarian cancer (i.e., a positive predictive value (PPV) of at least 10%). Skates et al. (2004) *J. Clin. Oncol.* 22:4059-4066. PPV is highly dependent upon the prevalence rates for a particular disease or condition and will shift dramatically as a result of differences in disease prevalence. Therefore, with low-prevalence diseases, such as ovarian cancer, screening diagnostic tests with a relatively low PPV still have significant clinical utility. Potential ovarian cancer screening programs must be adjusted for the low prevalence of ovarian cancer and assessed for biomarker performance and clinical need. See, for example, Skates et al. (2004) *J. Clin. Oncol.* 22:4059-4066; Bast et al. (2005) *Int. J. Gynecol. Cancer* 15:274-281; and Rosen et al. (2005) *Gyn. Oncol.* 99:267-277. Despite efforts to identify a biomarker or panel of biomarkers for the detection, particularly early detection, of ovarian cancer, no adequate screening or diagnostic test that satisfies clinical needs currently exists. Currently available methods, such as detection of CA125, exhibit unacceptably high false-positive rates.

The current recommendations from the National Cancer Institute state that "there is insufficient evidence to establish that screening for ovarian cancer with serum markers such as CA125, transvaginal ultrasound or pelvic examinations would result in a decrease in mortality from ovarian cancer" (*NCI Summary of Evidence (Level 4, 5)*; dated February 2005). In light of the serious risk of false-positives with currently available screening techniques, the NCI has not supported institution of general screening procedures for ovarian cancer. As such, no standardized screening test exists for ovarian cancer.

The 5-year survival rate for ovarian cancer, for example epithelial ovarian cancer (EOC), depends greatly on the stage of the disease at the time of diagnosis; increased survival is associated with early detection (i.e., Stage 1 or 2). The vast majority of ovarian cancers, however, are not diagnosed until stage 3 or 4, when prognosis is poor. Therefore, there is a need to identify more ovarian cancers at an earlier stage. The characterization of biomarkers that permit earlier identification of ovarian cancers has the potential to improve the clinical outcome for many patients. One such candidate biomarker is human epididymis protein 4 (HE4). HE4 is a secreted and glycosylated protein that was first observed in human epididymis tissue and is overexpressed in certain cancers, including ovarian and breast cancers. Subsequent studies have shown that HE4 protein is also present in the female reproductive tract and other epithelial tissues. The HE4 gene resides on human chromosome 20q12-13.1, and the 20q12 chromosome region has been found to be frequently amplified in ovarian carcinomas. See, for example, Bouchard et al. (2006) at oncology.thelancet.com 7:167-174; Galagono et al. (2006) *Mod. Patholo.* 19:847-583; Drapin et al. (2005) *Cancer Research* 65(6): 2162-9; Lu et al. (2004) *Clin. Cancer Res.* 10:3291-3300; Hellström et al. (2003) *Cancer Research* 63: 3695-3700; and Bingle et al. (2002) *Oncogene* 21: 2768-2773, all of which are herein incorporated by reference in their entirety. Accordingly, overexpression of HE4 in ovarian cancer cells suggests that this protein could be used as a biomarker in methods for detecting ovarian cancer or for identifying patients having an increased likelihood of having ovarian cancer.

In light of the above, a need exists in the art for antibodies that are capable of detecting expression of biomarkers, such as HE4, the overexpression of which may be indicative of ovarian cancer or an increased likelihood of a patient having ovarian cancer. Such antibodies could be used in methods for diagnosing ovarian cancer or for identifying patients having an increased likelihood of having ovarian cancer.

SUMMARY OF THE INVENTION

Compositions and methods for diagnosing ovarian cancer and for identifying patients with an increased likelihood of having ovarian cancer are provided. Compositions include monoclonal antibodies capable of binding to human epididymis protein 4 (HE4). Antigen-binding fragments and variants of these monoclonal antibodies, hybridoma cell lines capable of producing these antibodies, and kits comprising the monoclonal antibodies of the invention are also encompassed herein.

The compositions of the invention find use in methods for diagnosing cancer and in screening methods for identifying patients with an increased likelihood of having ovarian cancer. The methods for diagnosing ovarian cancer in a patient generally comprise detecting overexpression of HE4 protein in a patient body sample via a two-antibody or "sandwich" ELISA technique, as described herein. Screening methods for identifying patients with an increased likelihood of having ovarian cancer generally comprise detecting in a patient body sample expression of a plurality of biomarkers that are selectively overexpressed in ovarian cancer. Overexpression of the biomarkers is indicative of an increased likelihood that the patient has ovarian cancer. The methods of the invention may comprise, for example, a "two-step" analysis, wherein a first assay step is performed to detect the expression of a first biomarker (e.g., HE4) or panel of biomarkers. If the first biomarker or panel of biomarkers is overexpressed, a second assay step is performed to detect the expression of a second biomarker or panel of biomarkers. Overexpression of the first and second biomarkers or panels of biomarkers is indicative of an increased likelihood that the patient has ovarian cancer. The methods of the invention may utilize the disclosed HE4 antibodies to detect expression of HE4 in a patient sample. The compositions and methods of the invention may be further utilized in the diagnosis or detection of other types of cancer, including but not limited to breast cancer.

Compositions of the invention further include isolated polypeptides that comprise an epitope capable of binding an HE4 monoclonal antibody. These polypeptides find use in methods for producing HE4 antibodies. Isolated nucleic acid molecules encoding the amino acid sequences of the HE4 epitopes are also provided.

DETAILED DESCRIPTION OF THE INVENTION

Figure 1A:
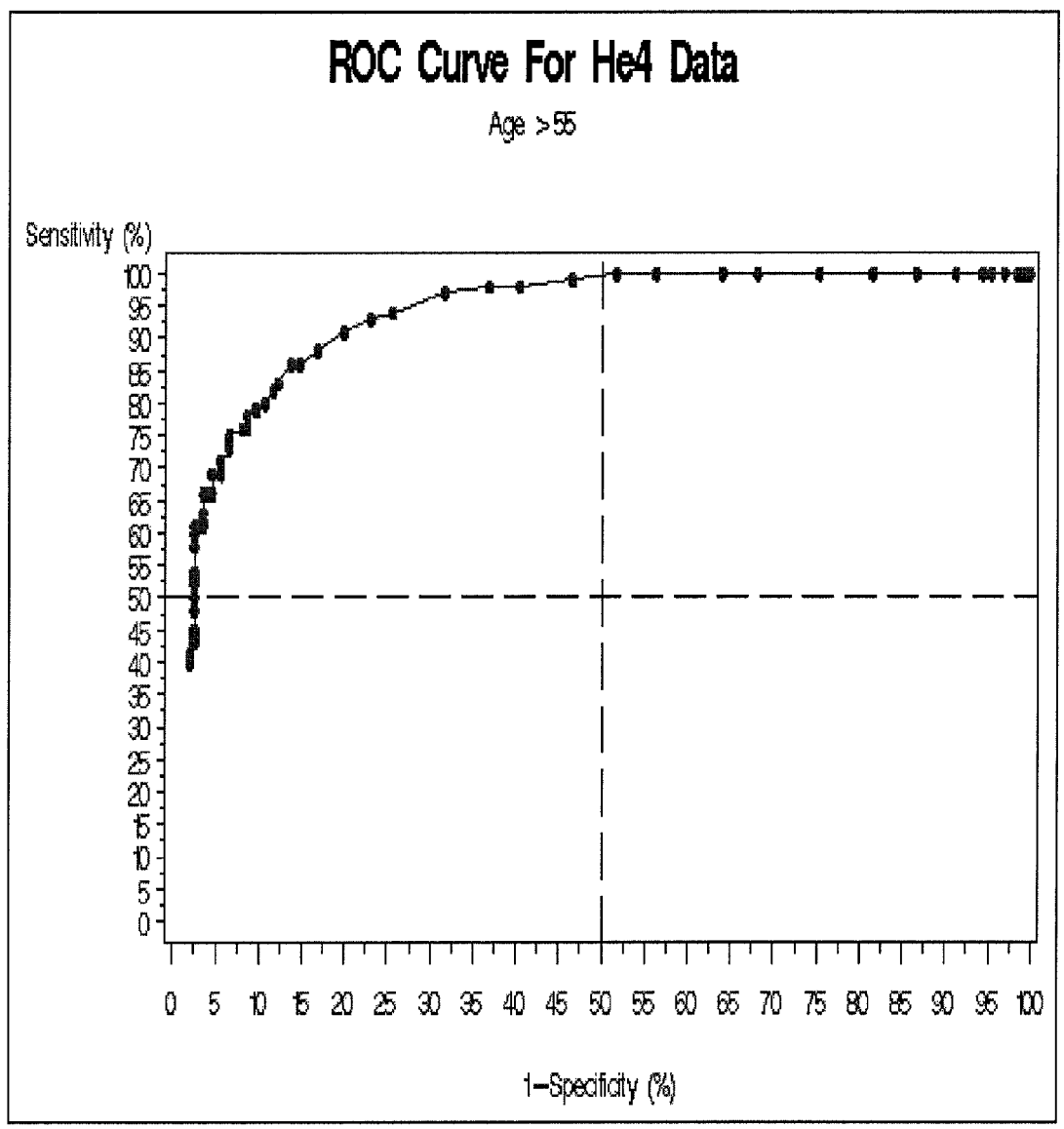
FIG. 1 provides the Receiver Operating Characteristic (ROC) plots for HE4 obtained with samples from patients over the age of 55 (A) and with patient samples of various ages (B) using the HE4 monoclonal antibodies designated as 363A90.1 and 363A71.1 in the sandwich ELISA assay described herein below.

Compositions and methods for diagnosing ovarian cancer in a patient and for identifying patients with an increased likelihood of having ovarian cancer are provided. Compositions include monoclonal antibodies that are capable of binding to HE4, a protein that has been shown to be overexpressed in ovarian cancer cells. Hybridoma cell lines that produce the monoclonal antibodies of the present invention are also disclosed. Kits comprising the monoclonal antibodies described herein are further provided. The present compositions find particular use in "sandwich" ELISA methods for diagnosing ovarian cancer in a patient and in screening methods for identifying patients with an increased likelihood of having ovarian cancer, as described in detail below.

The compositions of the invention include monoclonal antibodies that specifically bind to HE4, or to a variant or fragment thereof. In particular, the HE4 antibodies designated as 363A90.1 and 363A71.1 are provided. Hybridoma cell lines that produce HE4 monoclonal antibodies 363A90.1 and 363A71.1 were deposited with the Patent Depository of the American Type Culture Collection (ATCC), Manassas, Va., 20110-2209 on Feb. 2, 2007 and assigned Patent Deposit Nos. PTA-8196 and PTA-8195, respectively. These deposits will be maintained under the terms of the Budapest Treaty on the International Recognition of the Deposit of Microorganisms for the Purposes of Patent Procedure. Access to these deposits will be available during the pendency of the application to the Commissioner of Patents and Trademarks and persons determined by the Commissioner to be entitled thereto upon request. Upon allowance of any claims in the application, the Applicants will make available to the public, pursuant to 37 C.F.R. §1.808, sample(s) of the deposits with the ATCC. The deposits will be replaced by the Applicants if viable samples cannot be dispensed by the ATCC. These deposits were made merely as a convenience for those of skill in the art and are not an admission that a deposit is required under 35 U.S.C. §112.

Antibodies that have the binding characteristics of monoclonal antibodies 363A90.1 and 363A71.1 are also disclosed herein. Such antibodies include, but are not limited to, antibodies that compete in competitive binding assays with these antibodies, as well as antibodies that bind to an epitope capable of binding monoclonal antibody 363A90.1 or 363A71.1. Variants and fragments of monoclonal antibodies 363A90.1 and 363A71.1 that retain the ability to specifically bind to HE4 are also provided. Compositions further include hybridoma cell lines that produce the monoclonal antibodies of the present invention and kits comprising at least one monoclonal antibody disclosed herein.

"Antibodies" and "immunoglobulins" (Igs) are glycoproteins having the same structural characteristics. While antibodies exhibit binding specificity to an antigen, immunoglobulins include both antibodies and other antibody-like molecules that lack antigen specificity. Polypeptides of the latter kind are, for example, produced at low levels by the lymph system and at increased levels by myelomas.

The terms "antibody" and "antibodies" broadly encompass naturally occurring forms of antibodies and recombinant antibodies such as single-chain antibodies, chimeric and humanized antibodies and multi-specific antibodies as well as fragments and derivatives of all of the foregoing, which fragments and derivatives have at least an antigenic binding site. Antibody derivatives may comprise a protein or chemical moiety conjugated to the antibody. The term "antibody" is used in the broadest sense and covers fully assembled antibodies, antibody fragments that can bind antigen (e.g., Fab', F'(ab)$_2$, Fv, single chain antibodies, diabodies), and recombinant peptides comprising the foregoing. As used herein, "HE4 antibody" refers to any antibody that specifically binds to any HE4 isoform, particularly HE4 isoform T1 (SEQ ID NO:1), or to a variant or fragment thereof, and includes monoclonal antibodies, polyclonal antibodies, single-chain antibodies, and fragments thereof which retain the antigen binding function of the parent antibody. Five isoforms of the HE4 protein are known, designated T1-T5, as detailed in Table 1 below. One of skill in the art will appreciate that an HE4 monoclonal antibody of the invention may bind to more than one HE4 isoform so long as each isoform includes the relevant epitope sequence for the particular HE4 antibody.

TABLE 1

| HE4 Isoforms | | |
|---|---|---|
| HE4 Isoform | Accession No. | Sequence Identifier |
| T1 | NP_006094 | SEQ ID NO: 1 |
| T2 | NP_542774 | SEQ ID NO: 3 |
| T3 | NP_542771 | SEQ ID NO: 5 |
| T4 | NP_542772 | SEQ ID NO: 7 |
| T5 | NP_542773 | SEQ ID NO: 9 |

The HE4 antibodies of the invention are optimally monoclonal antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (V,) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity determining regions (CDRs) or hypervariable regions both in the light chain and the heavy-chain variable domains. The more highly conserved portions of variable domains are called the framework (FR) regions. The variable domains of native heavy and light chains each comprise four FR regions, largely adopting a p-sheet configuration, connected by three CDRs, which form loops connecting, and 15 in some cases forming part of, the p-sheet structure. The CDRs in each chain are held together in close proximity: by the FR regions and, with the CDRs from the other chain, contribute to the formation of the antigen-binding site: of antibodies (see Kabat et al., NIH Publ. No. 91-3242, Vol. I, pages 647-669 (1991)).

The constant domains are not involved directly in binding an antibody to an antigen, but exhibit various effecter functions, such as participation of the antibody in antibody-dependent cellular toxicity.

The term "hypervariable region" when used herein refers to the amino acid residues of an antibody which: are responsible for antigen-binding. The hypervariable region comprises amino acid residues from a "complementarily determining region" or "CDR" (i.e., residues 24-34 (L1), 50-56 (L2), and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institute of Health, 25 Bethesda, Md. [1991]) and/or those residues from a "hypervariable loop" (i.e., residues 26-32 (L1), 50-52 (L2) and 91-96 (L3) in the light chain variable domain and 2632 (H1), 53-55 (H2) and 96-101 (H3) in the heavy chain variable domain; Clothia and Lesk, *J. Mol. Biol.*, 196:901-917 [1987]). "Framework" or "FR" residues are those variable domain residues other than the hypervariable region residues as herein deemed.

"Antibody fragments" comprise a portion of an intact antibody, preferably the antigen-binding or variable region of the intact antibody. Examples of antibody fragments include Fab, Fab', F(ab')2, and Fv fragments; diabodies; linear antibodies (Zapata et al. (1995) *Protein Eng.* 8(10):1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. In a two-chain Fv species, this region consists of a dimer of one heavy- and one light-chain variable domain in tight, non-covalent association. In a single-chain Fv species, one heavy- and one light-chain variable domain can be covalently linked by flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them.

Fragments of the HE4 antibodies are encompassed by the invention so long as they retain the desired affinity of the full-length antibody. Thus, for example, a fragment of an HE4 antibody will retain the ability to bind to an HE4 antigen. Such fragments are characterized by properties similar to the corresponding full-length antibody, that is, the fragments will specifically bind HE4. Such fragments are referred to herein as "antigen-binding" fragments.

Suitable antigen-binding fragments of an antibody comprise a portion of a full-length antibody, generally the antigen-binding or variable region thereof. Examples of antibody fragments include, but are not limited to, Fab, $F(ab')_2$, and Fv fragments and single-chain antibody molecules. By "Fab" is intended a monovalent antigen-binding fragment of an immunoglobulin that is composed of the light chain and part of the heavy chain. By $F(ab')_2$ is intended a bivalent antigen-binding fragment of an immunoglobulin that contains both light chains and part of both heavy chains. By "single-chain Fv" or "sFv" antibody fragments is intended fragments comprising the $V_H$ and $V_L$ domains of an antibody, wherein these domains are present in a single polypeptide chain. See, for example, U.S. Pat. Nos. 4,946,778, 5,260,203, 5,455,030, and 5,856,456, herein incorporated by reference. Generally, the Fv polypeptide further comprises a polypeptide linker between the $V_H$ and $V_L$ domains that enables the sFv to form the desired structure for antigen binding. For a review of sFv see Pluckthun (1994) in *The Pharmacology of Monoclonal Antibodies*, Vol. 113, ed. Rosenburg and Moore (Springer-Verlag, New York), pp. 269-315.

Antibodies or antibody fragments can be isolated from antibody phage libraries generated using the techniques described in, for example, McCafferty et al. (1990) *Nature* 348:552-554 (1990) and U.S. Pat. No. 5,514,548. Clackson et al. (1991) *Nature* 352:624-628 and Marks et al. (1991) *J. Mol. Biol.* 222:581-597 describe the isolation of murine and human antibodies, respectively, using phage libraries. Subsequent publications describe the production of high affinity (nM range) human antibodies by chain shuffling (Marks et al. (1992) *Bio/Technology* 10:779-783), as well as combinatorial infection and in vivo recombination as a strategy for constructing very large phage libraries (Waterhouse et al. (1993) *Nucleic. Acids Res.* 21:2265-2266). Thus, these techniques are viable alternatives to traditional monoclonal antibody hybridoma techniques for isolation of monoclonal antibodies.

Various techniques have been developed for the production of antibody fragments. Traditionally, these fragments were derived via proteolytic digestion of intact antibodies (see, e.g., Morimoto et al. (1992) *Journal of Biochemical and Biophysical Methods* 24:107-117 (1992) and Brennan et al. (1985) *Science* 229:81). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al. (1992) *Bio/Technology* 10:163-167). According to another approach, F(ab')$_2$ fragments can be isolated directly from recombinant host cell culture. Other techniques for the production of antibody fragments will be apparent to the skilled practitioner.

Preferably antibodies of the invention are monoclonal in nature. As indicated above, "monoclonal antibody" is intended an antibody obtained from a population of substantially homogeneous antibodies, i.e., the individual antibodies comprising the population are identical except for possible naturally occurring mutations that may be present in minor amounts. The term is not limited regarding the species or source of the antibody. The term encompasses whole immunoglobulins as well as fragments such as Fab, F(ab')2, Fv, and others which retain the antigen binding function of the antibody. Monoclonal antibodies are highly specific, being directed against a single antigenic site, i.e., a particular epitope within the HE4 protein, as defined herein below. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, e.g., U.S. Pat. No. 4,816,567). The "monoclonal antibodies" may also be isolated from phage antibody libraries using the techniques described in, for example, Clackson et al. (1991) *Nature* 352:624-628; Marks et al. (1991) *J. Mol. Biol.* 222:581-597; and U.S. Pat. No. 5,514,548.

Monoclonal antibodies can be prepared using the method of Kohler et al. (1975) *Nature* 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen (i.e., antibody-producing cells) bind to the plate and are not rinsed away. Resulting B cells, or all dissociated spleen cells, are then induced to fuse with myeloma cells to form monoclonal antibody-producing hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice). Monoclonal antibodies can also be produced using Repetitive Immunizations Multiple Sites technology (RIMMS). See, for example, Kilpatrick et al. (1997) *Hybridoma* 16(4):381-389; Wring et al. (1999) *J. Pharm. Biomed. Anal.* 19(5):695-707; and Bynum et al. (1999) *Hybridoma* 18(5):407-411, all of which are herein incorporated by reference in their entirety.

As an alternative to the use of hybridomas, antibody can be produced in a cell line such as a CHO cell line, as disclosed in U.S. Pat. Nos. 5,545,403; 5,545,405; and 5,998,144; incorporated herein by reference. Briefly the cell line is transfected with vectors capable of expressing a light chain and a heavy chain, respectively. By transfecting the two proteins on separate vectors, chimeric antibodies can be produced. Another advantage is the correct glycosylation of the antibody. A monoclonal antibody can also be identified and isolated by screening a recombinant combinatorial immunoglobulin library (e.g., an antibody phage display library) with a biomarker protein to thereby isolate immunoglobulin library members that bind the biomarker protein. Kits for generating and screening phage display libraries are commercially available (e.g., the Pharmacia Recombinant Phage Antibody System, Catalog No. 27-9400-01; and the Stratagene SurfZAP$^9$ Phage Display Kit, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Antibodies having the binding characteristics of a monoclonal antibody of the invention are also provided. "Binding characteristics" or "binding specificity" when used in reference to an antibody means that the antibody recognizes the same or similar antigenic epitope as a comparison antibody. Examples of such antibodies include, for example, an antibody that competes with a monoclonal antibody of the invention in a competitive binding assay. One of skill in the art could determine whether an antibody competitively interferes with another antibody using standard methods.

By "epitope" is intended the part of an antigenic molecule to which an antibody is produced and to which the antibody will bind. An "HE4 epitope" comprises the part of the HE4 protein (or particular isoform thereof) to which an HE4 monoclonal antibody binds. Epitopes can comprise linear amino acid residues (i.e., residues within the epitope are arranged sequentially one after another in a linear fashion), nonlinear amino acid residues (referred to herein as "nonlinear epitopes"; these epitopes are not arranged sequentially), or both linear and nonlinear amino acid residues. Typically epitopes are short amino acid sequences, e.g. about five amino acids in length. Systematic techniques for identifying epitopes are known in the art and are described, for example, in U.S. Pat. No. 4,708,871 and in the examples set forth below. Briefly, in one method, a set of overlapping oligopeptides derived from the antigen may be synthesized and bound to a solid phase array of pins, with a unique oligopeptide on each pin. The array of pins may comprise a 96-well microtiter plate, permitting one to assay all 96 oligopeptides simultaneously, e.g., for binding to a biomarker-specific monoclonal antibody. Alternatively, phage display peptide library kits (New England BioLabs) are currently commercially available for epitope mapping. Using these methods, the binding affinity for every possible subset of consecutive amino acids may be determined in order to identify the epitope that a given antibody binds. Epitopes may also be identified by inference when epitope length peptide sequences are used to immunize animals from which antibodies are obtained.

The invention also encompasses isolated polypeptides comprising an epitope for binding an HE4 monoclonal antibody. These polypeptides correspond to a portion of the antigen (i.e., HE4) that binds to a monoclonal antibody. Such polypeptides find use in methods for producing antibodies that bind selectively to HE4. The ability of a polypeptide to be used in the production of antibodies is referred to herein as "antigenic activity." For example, the amino acid sequences set forth in SEQ ID NOs: 11, 12, and 13 (corresponding to residues 83 to 94, 93-116, and 93-112, respectively, in the HE4 isoform 1 amino acid sequence set forth in SEQ ID NO:1) comprise epitopes recognized by HE4 monoclonal antibodies, more particularly monoclonal antibodies 363A90.1 and 363A71.1. See Example 4 for details. Variants and fragments of the HE4 epitope sequences set forth in SEQ ID NOs: 11, 12, and 13 that retain the antigenic activity of the original polypeptide are also provided. The invention further includes isolated nucleic acid molecules that encode polypeptides that comprise HE4 epitopes, and variants and fragments thereof.

The polypeptides of the invention comprising HE4 epitopes can be used in methods for producing monoclonal antibodies that specifically bind to HE4, as described herein above. Such polypeptides can also be used in the production of polyclonal HE4 antibodies. For example, polyclonal antibodies can be prepared by immunizing a suitable subject (e.g., rabbit, goat, mouse, or other mammal) with a polypeptide comprising an HE4 epitope (i.e., an immunogen). The antibody titer in the immunized subject can be monitored over time by standard techniques, such as with an enzyme linked immunosorbent assay (ELISA) using immobilized biomarker protein. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77-96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.,* 54:387-402).

Amino acid sequence variants of a monoclonal antibody or a polypeptide comprising an HE4 epitope described herein are also encompassed by the present invention. Variants can be prepared by mutations in the cloned DNA sequence encoding the antibody of interest. Methods for mutagenesis and nucleotide sequence alterations are well known in the art. See, for example, Walker and Gaastra, eds. (1983) Techniques in Molecular Biology (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

In constructing variants of the polypeptide of interest, modifications are made such that variants continue to possess the desired activity, i.e., similar binding affinity to the biomarker (i.e., HE4). Obviously, any mutations made in the DNA encoding the variant polypeptide must not place the sequence out of reading frame and preferably will not create complementary regions that could produce secondary mRNA structure. See EP Patent Application Publication No. 75,444.

Preferably, variants of a reference polypeptide have amino acid sequences that have at least 70% or 75% sequence identity, preferably at least 80% or 85% sequence identity, more preferably at least 90%, 91%, 92%, 93%, 94% or 95% sequence identity to the amino acid sequence for the reference antibody molecule, or to a shorter portion of the reference antibody molecule. More preferably, the molecules share at least 96%, 97%, 98%, 99% or more sequence identity. For purposes of the present invention, percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482-489. A variant may, for example, differ from the reference antibody by as few as 1 to 15 amino acid residues, as few as 1 to 10 amino acid residues, such as 6-10, as few as 5, as few as 4, 3, 2, or even 1 amino acid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for sequence identity associated with conservative residue substitutions or gaps can be made (see Smith-Waterman homology search algorithm).

The HE4 monoclonal antibodies of the invention may be labeled with a detectable substance to facilitate biomarker protein detection in the sample, particularly for use in the sandwich ELISA methods disclosed herein below. Such antibodies find use in practicing the methods of the invention. The antibodies and antibody fragments of the invention can be coupled to a detectable substance to facilitate detection of antibody binding. The word "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable. Examples of detectable substances for purposes of labeling antibodies include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/ biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

The compositions of the invention find particular use in methods for diagnosing ovarian cancer in a patient. "Diagnosing ovarian cancer" is intended to include, for example, diagnosing or detecting the presence of ovarian cancer, monitoring the progression of the disease, and identifying or detecting cells or samples that are indicative of ovarian cancer. The terms diagnosing, detecting, and identifying ovarian cancer are used interchangeably herein. "Ovarian cancer" includes all stages of the disease (i.e., stages 1-4).

In one embodiment of the invention, a two antibody or "sandwich" ELISA is used to diagnose ovarian cancer in a patient by detecting overexpression of HE4 in a patient body sample. Such "sandwich" or "two-site" immunoassays are known in the art. See, for example, Current Protocols in Immunology. *Indirect Antibody Sandwich ELISA to Detect Soluble Antigens*, John Wiley & Sons, 1991. As used herein, "body sample" refers to any sampling of cells, tissues, or bodily fluids from a patient in which expression of a biomarker can be detected. Examples of such body samples include but are not limited to blood (e.g., whole blood, blood serum, blood having platelets removed, etc.), lymph, ascitic fluids, urine, gynecological fluids (e.g., ovarian, fallopian, and uterine secretion, menses, etc.), biopsies, fluids and tissues from a laparotomy, and ovarian tissue samples. Body samples may be obtained from a patient by a variety of techniques including, for example, by venipuncture, by scraping or swabbing an area, or by using a needle to aspirate bodily fluids or tissues. Methods for collecting various body samples are well known in the art. In particular embodiments, the body sample comprises blood or serum.

In the present sandwich ELISA methods, two antibodies specific to two distinct antigenic sites on HE4 are used, such as, for example, the HE4 monoclonal antibodies designated 363A90.1 and 363A71.1. The first antibody, known as the "capture antibody," is immobilized on or bound to a solid support. For example, a capture antibody directed to HE4 may be covalently or noncovalently attached to a microtiter plate well, a bead, a cuvette, or other reaction vessel. In a particular embodiment, the capture antibody is bound to a microtiter plate well. Methods for attaching an antibody to a solid support are routine in the art. In certain embodiments, the patient body sample, particularly a blood sample, more particularly a serum sample, is contacted with the solid support and allowed to complex with the bound capture antibody. Unbound sample is removed, and a second antibody, known as the "detection" or "tag" antibody, is added to the solid support. The tag antibody is specific for a distinct antigenic site on the biomarker of interest (i.e., HE4) and is coupled to or labeled with a detectable substance, as described above. Such antibody labels are well known in the art and include various enzymes, prosthetic groups, fluorescent materials, luminescent materials, bioluminescent materials, and radioactive materials. In certain aspects of the invention, the tag antibody is coupled to horseradish peroxidase (HRP). Following incubation with the tag antibody, unbound sample is removed, and HE4 expression levels are determined by quantitating the level of labeled detection antibody bound to the solid support, which in turn correlates directly with the level of bound HE4. This quantitation step can be performed by a number of known techniques and will vary depending on the specific detectable substance coupled to the tag antibody.

The sandwich ELISA methods of the invention may further comprise comparing the level of bound HE4 protein in a patient body sample to a threshold level to determine if the patient has ovarian cancer. As used herein, "threshold level" refers to a level of HE4 expression above which a patient sample is deemed "positive" and below which the sample is classified as "negative" for the disease. A threshold expression level for a particular biomarker (e.g., HE4) may be based on compilations of data from normal patient samples (i.e., a normal patient population). For example, the threshold expression level may be established as the mean HE4 expression level plus two times the standard deviation, based on analysis of samples from patients who do not have ovarian cancer. One of skill in the art will appreciate that a variety of statistical and mathematical methods for establishing the threshold level of expression are known in the art.

One of skill in the art will further recognize that the capture and tag antibodies can be contacted with the body sample sequentially, as described above, or simultaneously. Furthermore, the tag antibody can be incubated with the body sample first, prior to contacting the sample with the immobilized capture antibody. When the HE4 monoclonal antibodies of the present invention are used in the sandwich ELISA methods disclosed herein, either the 363A90.1 or 363A71.1 antibody may be used as the capture or detection antibody. In one particular embodiment, the capture antibody is HE4 monoclonal antibody 363A90.1 and the detection antibody is the 363A71.1 antibody, more particularly an HRP-labeled 363A71.1 antibody. The antibodies of the invention may be used in any assay format to detect HE4, including but not limited to multiplex bead-based assays.

With respect to the sandwich ELISA format described above in which two antibodies for the same biomarker (i.e., HE4) are used, multi-step analyses were performed to identify particular antibody combinations or pairings and concentrations of these antibodies that produce the best results with respect to complementarity of the antibodies and signal-to-noise ratios. In order to obtain optimal results in a sandwich ELISA format, the capture and tag antibodies should have distinct antigenic sites. By "distinct antigenic site" is intended that the antibodies are specific for different sites on the biomarker protein of interest (i.e., HE4) such that binding of one antibody does not significantly interfere with binding of the other antibody to the biomarker protein. To identify such antibody pairings, various HE4 antibody clones were prepared and analyzed. Specifically, the optical density at 450 nm (OD450) was measured for each individual HE4 antibody clone and for each pair of antibody clones. A number of mathematical metrics were used in the evaluation of the relative pairing potential of the group of HE4 antibodies, including but not limited to "differential index (DI)" and "adjusted additivity index/maximum adjusted additivity index (AAI/AAIMax)." One of skill in the art will appreciate that additional logic and interpretation strategies were also applied to identify the best HE4 antibody pairings for use in the sandwich ELISA methods.

The DI metric used in the evaluation of HE4 antibodies to identify potential optimal antibody pairings was obtained by measuring the OD450 values of each antibody separately and the two antibodies as a mixture. The higher OD450 value obtained with one of the antibodies alone was subtracted from the OD450 value of the antibody mixture to obtain the DI. The DI is a measure of the complementarity of the two antibodies being evaluated. That is, if two antibodies are complementary and work well as a pair, then the highest OD450 value obtained with the mixture of antibodies should be equal to the sum of OD450 of the two antibodies when each is measured separately, as a good pairing would involve no steric hindrance or interference with each antibody in binding to the protein. If two antibodies are not complementary but are instead competing for the same binding site on the protein, the highest OD450 value obtained with the mixture of antibodies should be no greater than the highest OD450 value obtained when the antibodies are tested separately because the second, weaker binding antibody would not contribute any additional OD450 value to the mixture beyond the OD450 value that was obtained from the stronger binding antibody alone. In the case of two antibodies competing for the exact same binding site, the DI would have a value of zero. Antibodies that are not complementary are not suitable for use in the sandwich ELISA methods described above.

The AAI/AAIMax was another mathematical metric used to identify the best HE4 antibody pairings. The AAI value is represented by the following formula:

$$[A_{1+2}/[(A_1+A_2+\sqrt{(A_1-A_2)^2})/2]-1] \times 100 = AAI$$

The AAIMAX value is represented by the formula listed below:

$$[A_1+A_2/[(A_1+A_2+\sqrt{(A_1-A_2)^2})/2]-1] \times 100 = AAIMax$$

The AAI/AAIMax value was obtained by dividing the AAI value by the AAIMax value and multiplying this result by 100:

$$(AAI\ \text{value}/AAI\text{Max value}) \times 100 = AAI/\text{AAIMax}$$

Although additional reasoning techniques were applied to identify the best HE4 monoclonal antibody pairings, a low DI and a high AAI/AAIMax were factors considered in identifying the best potential pairings for further investigation, particularly for use in the sandwich ELISA method for diagnosing ovarian cancer in a patient.

Additional analyses were performed to confirm potentially good HE4 antibody pairings identified as described above. Specifically, potential HE4 monoclonal antibody pairings of interest were assayed in a buffer-based assay. Each antibody was assayed at various concentrations and alternately used as the capture or the labeled tag antibody. The monoclonal antibodies of the present invention, namely 363A90.1 and 363A71.1, were identified as a good pairing of the HE4 antibodies tested and were subjected, along with other antibody pairs, to further analysis. For example, the 363A90.1 and 363A71.1 antibodies were tested against serum samples spiked with purified HE4 protein. This and other pairs of HE4 antibodies were tested with these spiked HE4 samples, using each antibody as the capture and the tag antibody and at various concentrations to obtain the largest signal-to-noise ratio. Moreover, the best pairings of HE4 antibodies were also used to analyze sera from ovarian cancer patients and sera from post-menopausal, ovarian cancer-free donors in a sandwich ELISA to identify the antibody pairing that optimally differentiated ovarian cancer and normal samples. Although other antibody pairs displayed reasonable results with respect to complementarity and ability to differentiate normal and ovarian cancer samples, the pairing of HE4 monoclonal antibodies 363A90.1 and 363A71.1 was significantly better than the other antibody pairs analyzed. One of skill in the art will recognize that further optimization of antibody concentration, antibody incubation time, buffer conditions, and detection chemistry will be needed. The design of assays to optimize such conditions is standard and well within the routine capabilities of those of ordinary skill in the art.

The compositions of the invention find further use in screening methods for identifying patients with an increased likelihood of having ovarian cancer, such as those disclosed in pending U.S. application Ser. No. 11/699,229, entitled "Methods For Identifying Patients With An Increased Likelihood Of Having Ovarian Cancer And Compositions Therefor," filed Jan. 29, 2007, which is herein incorporated by reference in its entirety. As used herein, "identifying patients with an increased likelihood of having ovarian cancer" is intended methods for detecting those females that are more likely to have ovarian cancer. An "increased likelihood of having ovarian cancer" is intended to mean that patients who are determined in accordance with the present methods to exhibit overexpression of particular biomarkers are more likely to have ovarian cancer than those patients who do not.

The screening methods generally comprise detecting the expression of a plurality of biomarkers in a body sample, particularly a blood sample, more particularly a serum sample, from the patient. Overexpression of the biomarkers used in the practice of the invention is indicative of an increased likelihood of the presence of ovarian cancer. In particular screening methods of the invention, a two-step analysis is used to identify patients having an increased likelihood of having ovarian cancer. The first assay step is performed to detect the expression of a first biomarker or panel of biomarkers in a patient body sample. In particular embodiments, the first biomarker is HE4. One or more of the HE4 monoclonal antibodies of the present invention may be used to practice the ovarian cancer screening methods. If the first biomarker or panel of biomarkers is determined to be overexpressed in the sample, a second assay step is performed to detect the expression of a second biomarker or panel of biomarkers. In certain aspects of the invention, the second biomarker of panel of biomarkers is selected from the group consisting of a panel comprising CA125, glycodelin, Muc-1, PAI-1, and PLAU-R, a panel comprising CA125 and PAI-1, a panel comprising CA125, glycodelin, PAI-1, and MMP-7, a panel comprising CA125, glycodelin, PAI-1, and PLAU-R, a panel comprising CA125, glycodelin, PAI-1, and PLAU-R, a panel comprising glycodelin, Muc-1, PLAU-R, and inhibin A, a panel comprising CA125, Muc-1, glycodelin, PAI-1, and PLAU-R, and a panel comprising CA125, MMP-7, glycodelin, and PLAU-R. Overexpression of the first and second biomarkers or panels of biomarkers is indicative of an increased likelihood that the patient has ovarian cancer.

The level of expression of a particular biomarker that is sufficient to constitute "overexpression" in the screening methods of the invention will vary depending on the specific biomarker used. In particular embodiments of the invention, a "threshold level" of expression is established for a particular biomarker, wherein expression levels above this value are deemed overexpression. A variety of statistical and mathematical methods for establishing the threshold level of expression are known in the art. A threshold expression level for a particular biomarker may be selected, for example, based on data from Receiver Operating Characteristic (ROC) plots or on compilations of data from normal patient samples (i.e., a normal patient population). For example, the threshold expression level may be established at the mean expression level plus two times the standard deviation, based on analysis of samples from normal patients not afflicted with ovarian cancer. One of skill in the art will appreciate that these threshold expression levels can be varied, for example, by moving along the ROC plot for a particular biomarker, to obtain different values for sensitivity, specificity, positive predictive value (PPV), and negative predictive value (NPV), thereby affecting overall assay performance.

In a particular aspect of the invention, the first assay step of the present methods for identifying patients with an increased likelihood of having ovarian cancer comprise obtaining a blood sample, particularly a serum sample from a patient, contacting the sample with at least one HE4 monoclonal antibody of the invention, and detecting binding of the antibody to HE4. In other embodiments, the sample is contacted with at least two monoclonal antibodies that specifically bind to HE4, particularly monoclonal antibodies 363A90.1 and 363A71.1. Samples that exhibit overexpression of HE4 are analyzed further for expression of a second biomarker or panel of biomarkers of interest. Overexpression of HE4 and the second biomarker or panel of biomarkers is indicative of an increased likelihood of the patient having ovarian cancer. Techniques for detecting antibody-antigen binding are well known in the art. Antibody binding to a biomarker of interest may be detected through the use of chemical reagents that generate a detectable signal that corresponds to the level of antibody binding and, accordingly, to the level of biomarker protein expression. Any method for detecting antibody-antigen binding may used to practice the methods of the invention.

Other HE4 antibodies, including monoclonal antibodies, are known in the art. Monoclonal antibodies 363A90.1 and 363A71.1, however, exhibit superior properties in the methods of diagnosing ovarian cancer in a patient and in the screening methods for identifying patients having an increased likelihood of having ovarian cancer, as described in the present application. Accordingly, the pairing of monoclonal antibodies of 363A90.1 and 363A71.1 is particularly powerful in the diagnosis of and screening for increased likelihood of having ovarian cancer.

The efficacy of the methods disclosed herein may be assessed by determining such measures as sensitivity, specificity, positive predictive (PPV), and negative predictive value (NPV). As used herein, "specificity" refers to the proportion of disease negatives that are test-negative. In a clinical study, specificity is calculated by dividing the number of true negatives by the sum of true negatives and false positives. By "sensitivity" is intended the level at which a method of the invention can accurately identify samples that have been confirmed as positive (i.e., true positives). Thus, sensitivity is the proportion of disease positives that are test-positive. Sensitivity is calculated in a clinical study by dividing the number of true positives by the sum of true positives and false negatives. In some embodiments, the sensitivity of the disclosed methods for diagnosing ovarian or cancer or for identifying patients with an increased likelihood of having ovarian cancer is preferably at least about 70%, more preferably at least about 80%, most preferably at least about 90, 91, 92, 93, 94, 95, 96, 97, 98, 99% or more. Furthermore, the specificity of the present methods is preferably at least about 70%, more preferably at least about 80%, most preferably at least about 90, 91, 92, 93, 94, 95, 96, 97, 98, 99% or more.

The term "positive predictive value" or "PPV" refers to the probability that a patient has the disease of interest (e.g., ovarian cancer) restricted to those patients who are classified as positive using a method of the invention. PPV is calculated in a clinical study by dividing the number of true positives by the sum of true positives and false positives. The "negative predictive value" or "NPV" of a test is the probability that the patient will not have the disease when restricted to all patients who test negative. NPV is calculated in a clinical study by dividing the number of true negatives by the sum of true negatives and false negatives.

Kits comprising at least one HE4 monoclonal antibody of the invention are further provided. By "kit" is intended any manufacture (e.g., a package or a container) comprising at least one reagent, i.e., an antibody, for specifically detecting the expression of HE4. The kit may be promoted, distributed, or sold as a unit for performing the methods of the present invention. Furthermore, any or all of the kit reagents may be provided within containers that protect them from the external environment, such as in sealed containers. The kits may also contain a package insert describing the kit and methods for its use.

Kits for performing the sandwich ELISA methods of the invention generally comprise a capture antibody, optionally immobilized on a solid support (e.g., a microtiter plate), and a tag antibody coupled with a detectable substance, such as, for example HRP, a fluorescent label, a radioisotope, β-galactosidase, and alkaline phosphatase. In certain embodiments, the capture antibody and the tag antibody are monoclonal antibodies, particularly HE4 monoclonal antibodies, more particularly the HE4 monoclonal antibodies designated 363A90.1 and 363A71.1. In one kit of the invention for practicing the sandwich ELISA method, the capture antibody is HE4 monoclonal antibody 363A90.1, immobilized on a microtiter plate, and the tag antibody is HRP-labeled 363A71.1. Chemicals for detecting and quantitating the level of tag antibody bound to the solid support (which directly correlates with the level of HE4 in the sample) may be optionally included in the kit. Purified HE4 may also be provided as an antigen standard.

Kits for performing the screening methods of the invention for identifying patients with an increased likelihood of having ovarian cancer generally comprise at least one monoclonal antibody directed to HE4, chemicals for the detection of antibody binding, a counterstain, and, optionally, a bluing agent to facilitate identification of positive staining cells. Any chemicals that detect antigen-antibody binding may be used in the kits of the invention. In some embodiments, the detection chemicals comprise a labeled polymer conjugated to a secondary antibody. For example, a secondary antibody that is conjugated to an enzyme that catalyzes the deposition of a chromogen at the antigen-antibody binding site may be provided. Such enzymes and techniques for using them in the detection of antibody binding are well known in the art. In one embodiment, the kit comprises a secondary antibody that is conjugated to an HRP-labeled polymer. Chromogens compatible with the conjugated enzyme (e.g., DAB in the case of an HRP-labeled secondary antibody) and solutions, such as hydrogen peroxide, for blocking non-specific staining may be further provided. The kits may further comprise a peroxidase blocking reagent (e.g., hydrogen peroxide), a protein blocking reagent (e.g., purified casein), and a counterstain (e.g., hematoxylin). A bluing agent (e.g., ammonium hydroxide or TBS, pH 7.4, with Tween-20 and sodium azide) may be further provided in the kit to facilitate detection of positive staining cells. Kits may also comprise positive and negative control samples for quality control purposes. Development of appropriate positive and negative controls is well within the routine capabilities of those of ordinary skill in the art.

In another embodiment, the kits of the invention comprise at least two HE4 monoclonal antibodies, more particularly monoclonal antibodies 363A90.1 and 363A71.1. When multiple antibodies are present in the kit, each antibody may be provided as an individual reagent or, alternatively, as an antibody cocktail comprising all of the antibodies of interest.

Although the above methods have been described for diagnosing ovarian cancer and for identifying patients with an increased likelihood of having ovarian cancer, one of skill in the art will recognize that the disclosed methods could be similarly applied to other cancers in which HE4 is overexpressed. Such cancers include but are not limited to breast cancer.

One of skill in the art will further appreciate that any or all of the steps in the methods of the invention could be implemented by personnel in a manual or automated fashion. Thus, the steps of sample preparation, antibody incubation, and detection of antibody binding may be automated. A patient that is identified as having ovarian cancer or an increased likelihood of having ovarian cancer in accordance with the disclosed methods may be subjected to further diagnostic testing to definitively determine if the patient has ovarian cancer. "Further diagnostic testing" includes but is not limited to pelvic examination, transvaginal ultrasound, CT scan, MRI, laparotomy, laparoscopy, and biopsy. Such diagnostic methods are well known in the art. Moreover, patients classified as having an increased likelihood of having ovarian cancer that are determined by further diagnostic testing not to currently have ovarian cancer may be closely monitored on a regular basis for the development of ovarian cancer. Monitoring of such patients may include but is not limited to periodic pelvic examination, transvaginal ultrasound, CT scan, and MRI. A physician of ordinary skill in the art will appreciate appropriate techniques for monitoring patients for the development of ovarian cancer.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

The following examples are offered by way of illustration and not by way of limitation:

EXPERIMENTAL

Example 1

Production of Mouse Monoclonal Antibodies to HE4

Mouse monoclonal antibodies specific for HE4 were generated. The antigen (an immunogenic polypeptide) was a full-length recombinant hexahistidine-tagged HE4 isoform 1 protein. The antigen was expressed using a baculovirus expression system in Tni cells. Specifically, the coding sequence for the hexahistidine-tagged HE4 was cloned into the pFastBac1 plasmid (Invitrogen) for expression in Tni cells. Methods for producing recombinant proteins using baculovirus expression systems are well known in the art. The tagged HE4 protein was purified using a chelating agarose charged with Ni+2 ions (Ni-NTA from Qiagen) and used as an immunogen. The amino acid and nucleotide sequences of the HE4 isoform 1 polypeptide are provided in SEQ ID NOs:1 and 2, respectively.

Mouse immunizations and hybridoma fusions were performed essentially as described in Kohler et al. (1975) *Nature* 256:495-496. Mice were immunized with the immunogenic tagged-HE4 protein in solution. Antibody-producing cells were isolated from the immunized mice and fused with myeloma cells to form monoclonal antibody-producing hybridomas. The hybridomas were cultured in a selective medium. The resulting cells were plated by serial dilution and assayed for the production of antibodies that specifically bind HE4 (and that do not bind to unrelated antigens). To confirm that the monoclonal antibodies of interest reacted with the HE4 protein only, selected hybridomas were screened against either a SLPI or Spon2-His tagged protein. Selected monoclonal antibody (mAb)-secreting hybridomas were then cultured.

Antibodies were purified from the culture media supernatants of "exhausted" hybridoma cells (i.e., cells grown until viability drops to between 0-15%) using recombinant Protein A-coated resin (STREAMLINE®, Amersham, Inc.). Antibodies were eluted using low pH followed by immediate neutralization of pH. Fractions with significant absorbances at 280 nM were pooled. The resultant pool was dialyzed against PBS. Purified antibodies were subjected to further characterization. HE4 monoclonal antibodies 363A90.1 and 363A71.1 were both produced in accordance with the above method. HE4 monoclonal antibodies 363A90.1 and 363A71.1 were determined to be $IgG_{2a}$ isotype and $IgG_1$ isotype, respectively. Details of the epitope mapping of these antibodies are described below.

Example 2

Isolation of Monoclonal Antibodies from Hybridoma Cells

The following procedure is used to isolate monoclonal antibodies from hybridoma cells:

Media Preparation

To a sterile 1,000 ml storage bottle, add 100 ml Hyclone Fetal Bovine Serum (FBS).

Add 10 ml of MEM Non-Essential Amino Acids Solution.

Add 10 ml of Penicillin-Streptomycin-L-Glutamine Solution.

QS to approximately 1000 ml with ExCell 610-HSF media.

Place sterile cap on bottle and secure tightly. Swirl gently to mix.

Connect a 1000 ml sterile acetate vacuum filter unit (0.2 μm) to a vacuum pump system.

Gently pour approximately half of the media solution into sterile acetate vacuum filter unit and turn on the vacuum.

Once the first half of the media has been filtered, pour the remaining media into the filter unit and continue filtering.

After all the media has been filtered, disconnect the vacuum hose from the vacuum filter unit and turn off the vacuum pump. Remove the receiver portion of the filter unit from the filter bottle. Place a new sterile bottle cap on the bottle.

Store at 2° C. to 10° C. Protect from light.

Initial Hybridoma Cell Culture

Thaw vial of stock hybridoma frozen culture in a prewarmed 37° C. $H_2O$ bath.

Spray the outside of the freeze vial with 70% ethanol.

Move the thawed vial into the Biological Safety Cabinet.

Remove the cells from the freeze vial and transfer the cells to a 15 ml centrifuge tube.

Add 7 ml of cell culture media drop-wise to the 15 ml centrifuge tube containing the thawed cells.

Centrifuge the 15 ml centrifuge tube containing the thawed cells and culture media for 5 minutes at 200 g force.

While the cells are in the centrifuge, add 45 ml of cell culture media to a sterile T-225 flask.

After centrifugation, visually inspect the tube for the presence of a cell pellet.

Remove the media from the centrifuge tube being careful not to dislodge the cell pellet. Note: If the cell pellet is disturbed, repeat the centrifugation step.

Add 5 ml of cell culture media to the 15 ml centrifuge tube containing the pelleted cells. Pipette to re-suspend the cell pellet into the media.

Transfer the entire contents of the resuspended cells and culture media into the T-225 flask containing the 45 ml of media.

Cap the T-225 flask.

Observe for presence of intact cells under the microscope. Place the T-225 flask immediately into a CO2 incubator and allow the cells to incubate overnight.

Expansion of Hybridoma Cell Line

Continue to monitor the cell culture for viability, concentration, and presence of contamination.

Monitor and adjust the cell suspension from the initial T-225 flask until the concentration is approximately 600,000 cells/ml to 800,000 cells/ml and a total of 200 to 250 ml of media.

Dislodge cells and add additional media as needed to meet minimum cell density requirements. Divide and transfer cell suspension into one new sterile T-225 flask. Place the 2×T-225 flasks into the CO2 incubator.

Monitor the cells from the 2×T-225 flasks until the concentration is approximately 600,000 cells/ml to 800,000 cells/ml, and a total of between 200 to 250 ml of media for each flask.

Dislodge cells and add additional media as needed to meet minimum cell density requirements. Divide and transfer the cell suspensions into 2 additional new sterile T-225 flasks for a total of 4×T-225 flasks. Return all flasks to the CO2 incubator.

Monitor the cells, and adjust volume in the 4×T-225 flasks until the cell concentration is approximately 600,000 cells/ml to 800,000 cells/ml with a total volume of approximately 250 ml per T-225 flask (or approximately 1000 ml total).

Continue to monitor the cells from the 4×T-225 flasks until the cells have grown to exhaustion, with a final viability of 0%-15%. The cell culture supernatant is now ready for the Clarification Process.

Clarification of Supernatant

Turn on the tabletop centrifuge. Place the 500 ml tube adapters into the rotor buckets, close the lid and set the temperature to 4° C. (+/−) 4° C.

Using aseptic technique, pour the media from all four of the now exhausted T-225 flasks into 2×500 ml conical centrifuge tubes.

Make sure the 2×500 ml tubes are balanced. Transfer supernatant from one tube to the other as necessary to balance them.

Centrifuge the exhausted supernatant at 1350 g (+/−40 g) for 15 minutes at 2° C. to 10° C.

After centrifugation is complete, aseptically decant the supernatant into a sterile 1000 ml storage bottle and secure with a sterile cap.

Aseptically transfer 1 ml to the microfuge tube. Store microfuge tube with sample at 2° C. to 10° C. (Protect from light).

The clarified supernatant sample is ready for IgG evaluation using the Easy-Titer® Assay.

Buffer Preparation

Binding Buffer:
Add approximately 600 ml of DI $H_2O$ to a clean beaker.
Add 77.28 ml of Boric Acid solution (4% W/V). Stir at room temperature with a clean stir bar.
Weigh out 233.76 g of Sodium Chloride and place into the solution while continuing to stir.
Bring solution up to approximately 950 ml with DI $H_2O$ and continue to stir.
When the Sodium Chloride has dissolved and the solution is clear, adjust the pH to 9.0±0.2 with Sodium Hydroxide.
Remove the solution to a clean 1000 ml graduated cylinder and QS to 1000 ml with DI $H_2O$.
Transfer the completed buffer to an appropriate storage bottle. This buffer may be stored for up to 7 days before use.
Repeat this entire process to prepare an additional 0.2 liters to 1.0 liter of Binding Buffer.

Elution Buffer
Weigh out 1.725 g of sodium phosphate, monobasic and place into a clean 250 ml beaker with a clean stir bar.
Weigh out 3.676 g of sodium citrate and place into the same clean 250 ml beaker.
Add approximately 175 ml of DI $H_2O$ and stir at room temperature until dissolved.
Weigh out 4.38 g of Sodium Chloride and place into the solution while continuing to stir.
Bring solution up to approximately 225 ml with DI $H_2O$ and continue to stir.
When the Sodium Chloride has dissolved and the solution is clear, adjust the pH to 3.5±0.2 with Hydrochloric Acid.
Remove the solution to a clean 250 ml graduated cylinder and QS to 250 ml with DI $H_2O$.
Connect a 500 ml sterile acetate vacuum filter unit (0.2 µm) to a vacuum pump system and filter sterilize the solution.
Remove the filter and close the container with a sterile cap.

Antibody Adsorption
Pour the Clarified Supernatant (~1 L) into a clean 4000 ml plastic beaker with a clean stir bar.
Add an approximately equal amount (~1 L) of the Binding Buffer to the clean 4000 ml plastic beaker containing the clarified supernatant. Add a clean stir bar.
Cover the beaker with clean plastic wrap and label "Antibody Binding."
Calculate the approximate amount of STREAMLINE® Protein A that will be needed using the data in Table 2.

TABLE 2

Volume of Protein A Resin Required

| Quantity IgG (µg/ml) in Supernatant | Volume of Protein A Resin Required in Milliliters (ml) |
|---|---|
| >180-≦200 | 12.0 |
| >160-≦180 | 11.0 |
| >140-≦160 | 10.0 |
| >120-≦140 | 9.0 |
| >100-≦120 | 8.0 |
| >80-≦100 | 7.0 |
| >60-≦80 | 6.0 |
| >40-≦60 | 4.5 |
| >20-≦40 | 3.5 |
| ≦20 | 2.0 |

Secure a clean Disposable Column and stopcock assembly to a ring stand and clamp. Close the stopcock.

Mix appropriate amount of STREAMLINE Protein A beads by inverting the bottle several times. Withdraw the required volume and place into the Disposable Column.

Wash the STREAMLINE Protein A beads with 10 ml of DI $H_2O$. Open the stopcock and allow the DI $H_2O$ to drain. Close the stopcock. Repeat with an additional 10 ml of DI $H_2O$.

Wash the STREAMLINE Protein A beads with 10 ml of Binding Buffer. Open the stopcock and allow the Binding Buffer to drain. Close the stopcock. Repeat with an additional 10 ml of Binding Buffer.

Resuspend the STREAMLINE Protein A beads in ~10 ml of the Clarified Supernatant and Binding Buffer solution (from the 4000 ml beaker) and transfer the beads into the 4000 ml beaker containing the Clarified Supernatant and Binding Buffer solution. Repeat as required to transfer any remaining beads. When completed, discard the column and stopcock.

Allow the mixture to mix vigorously at 2° C. to 10° C. for approximately 18 hours.

When mixing is complete, turn off the stir plate and remove the "Antibody Binding" beaker with the buffered supernatant and bead suspension back to the lab bench area. Allow the STREAMLINE Protein A beads to settle to the bottom of the beaker (approximately 5 minutes).

Secure a clean Disposable Column and stopcock assembly to a ring stand and clamp. Close the stopcock.

Label a clean, 250 ml bottle or suitable container "Column Wash-Post Binding."

Label a clean plastic beaker "Supernatant-Post Binding."

Decant the supernatant from the 4000 ml beaker into the clean, labeled, 2 liter plastic beaker, leaving the beads in the bottom of the 4000 ml beaker. Cover the 2000 ml beaker containing the "Supernatant-Post Binding" solution with clean plastic wrap and store at 2° C. to 10° C.

Add approximately 15 ml of Binding Buffer into the decanted 4000 ml "Antibody Binding" beaker. Resuspend the STREAMLINE Protein A beads and transfer them to the column. Open the stopcock and allow the Binding Buffer to drain into the "Column Wash-Post binding" container. Close the stopcock when drained.

Transfer any remaining STREAMLINE Protein A beads in the "Antibody Binding" beaker by adding additional Binding Buffer, mixing, and transferring to the column as in the preceding steps. Close the stopcock when drained.

Calculate the approximate amount of Binding Buffer needed to wash the STREAMLINE Protein A beads in the column using the data in Table 3.

TABLE 3

| Binding Buffer Volume for Column Wash | |
|---|---|
| Quantity IgG (µg/ml) in Supernatant | Volume of Binding Buffer Required in Milliliters (ml) |
| >180-≦200 | 5 column washes total with 15.0 ml each |
| >160-≦180 | 5 column washes total with 15.0 ml each |
| >140-≦160 | 5 column washes total with 12.5 ml each |
| >120-≦140 | 5 column washes total with 12.5 ml each |
| >100-≦120 | 5 column washes total with 12.5 ml each |
| >80-≦100 | 5 column washes total with 10.0 ml each |
| >60-≦80 | 5 column washes total with 10.0 ml each |
| >40-≦60 | 5 column washes total with 7.5 ml each |
| >20-≦40 | 5 column washes total with 5.0 ml each |
| ≦20 | 5 column washes total with 5.0 ml each |

Wash the STREAMLINE Protein A beads in the column with the appropriate volume of Binding Buffer for the appropriate number of washes, continuing to collect the effluent into the "Column Wash-Post Binding" container.

When completed, close the stopcock. Store the "Column Wash-Post Binding" container at 2° C. to 10° C.

Determine the Total Volumes of Elution Buffer and Neutralization Buffer needed to elute the STREAMLINE Protein A beads in the column from Table 4.

TABLE 4

| Determination of Amount of Elution Buffer and Neutralization Buffer | | | | |
|---|---|---|---|---|
| Quantity IgG (µg/ml) in Supernatant | Total Volume of Elution Buffer Required (ml) | Total Volume of Neutralization Buffer Required (ml) | Volume of Elution Buffer Required per fraction (ml) | Volume of Neutralization Buffer Required per fraction (ml) |
| >180-≦200 | 72 | 7.2 | 12 | 1.2 |
| >160-≦180 | 66 | 6.6 | 11 | 1.1 |
| >140-≦160 | 60 | 6.0 | 10 | 1.0 |
| >120-≦140 | 54 | 5.4 | 9 | 0.9 |
| >100-≦120 | 48 | 4.8 | 8 | 0.8 |
| >80-≦100 | 42 | 4.2 | 7 | 0.7 |
| >60-≦80 | 36 | 3.6 | 6 | 0.6 |
| >40-≦60 | 27 | 2.7 | 4.5 | 0.45 |
| >20-≦40 | 21 | 2.1 | 3.5 | 0.35 |
| ≦20 | 12 | 1.2 | 2 | 0.2 |

Label 9 sterile conical centrifuge tubes "Eluted Antibody", Fraction # (1 through 9).

Place the appropriate volume of Neutralization Buffer required per fraction (as determined from Table "C" above) into each of the 9 "Eluted Antibody" fraction tubes and place securely under the column stopcock outlet.

Elute the STREAMLINE Protein A beads in the column fraction by fraction with the appropriate volume of Elution Buffer required per fraction (as determined from Table 3 above) while collecting the eluate into each of the "Eluted Antibody" tubes containing Neutralization Buffer.

When the elutions are complete, mix each "Eluted Antibody" fraction tube gently by swirling several times. Remove approximately 50 μl of fraction # 3 and place on a pH test paper strip to ensure that the eluate has been neutralized to an approximate pH between 6.5 to 8.5. If required, add additional Neutralizing Buffer or Elution Buffer as needed to bring pH into range.

When pH evaluation is completed, perform an Absorbance Scan of a sample from each fraction at 280 nm-400 nm to determine the approximate concentration of IgG in the eluate prior to proceeding to the Dialysis Process.

Accept fractions as part of the Eluate Pool if the A280-A400 value is ≧0.200.

Reject fractions as part of the Eluate Pool if the A280-A400 value is <0.200.

Label a sterile conical centrifuge tube "Eluted Antibody," "Eluate Pool," and combine all fractions that were Accepted as part of the pool.

Perform an Absorbance Scan of a sample of the Eluate Pool to determine the approximate concentration of IgG in the eluate prior to proceeding to the Dialysis Process.

Estimate the volume of the Eluate Pool and calculate the approximate total mgs of IgG.

Volume of Eluate Pool: mls×IgG mg/ml=Total mgs of IgG

Antibody Dialysis

Remove the "Eluted Antibody" tube from 2° C. to 10° C.

Calculate the approximate length of Dialysis Tubing that will be needed to dialyze the antibody eluate using the approximate volume of eluate and the data in Table 5.

Cut the appropriate length of dialysis tubing required. (Spectra/Por® 2 Regenerated Cellulose Membrane, 12,000-14,000 Dalton Molecular Weight Cutoff (MWCO), 16 mm Diameter, Spectrum Laboratories Inc., Cat. No. 132678)

Hydrate the dialysis membrane tubing in 1000 ml of $DIH_2O$ for >30 minutes.

Calculate the approximate volume of Dialysis Buffer needed to dialyze the antibody eluate using the data in Table 6.

TABLE 6

Volume of Dialysis Buffer Required

| Quantity IgG (μg/ml) in Supernatant | Final Volume of Eluted Antibody in Milliliters (ml) | Length of Dialysis Tubing Needed (cm) | Volume of Dialysis Buffer (1 × PBS) Needed in Liters |
|---|---|---|---|
| >180-≦200 | 39.6 ml | 63 cm | 3 complete changes of 4.0 Liters |
| >160-≦180 | 36.3 ml | 59 cm | 3 complete changes of 3.6 Liters |
| >140-≦160 | 33.0 ml | 55 cm | 3 complete changes of 3.3 Liters |
| >120-≦140 | 29.7 ml | 51 cm | 3 complete changes of 3.0 Liters |
| >100-≦120 | 26.4 ml | 47 cm | 3 complete changes of 2.6 Liters |
| >80-≦100 | 23.1 ml | 43 cm | 3 complete changes of 2.3 Liters |
| >60-≦80 | 19.8 ml | 39 cm | 3 complete changes of 1.9 Liters |
| >40-≦60 | 14.85 ml | 33 cm | 3 complete changes of 1.5 Liters |
| >20-≦40 | 11.55 ml | 29 cm | 3 complete changes of 1.2 Liters |
| ≦20 | 6.6 ml | 23 cm | 3 complete changes of 0.7 Liters |

Place the appropriate amount of Dialysis Buffer into a suitable sized plastic beaker. Label the beaker "Dialyzed Antibody." Add a clean stir bar and place the beaker on a stir plate inside a refrigerator or cold room at 2° C. to 10° C.

TABLE 5

Calculation of Length of Dialysis Tubing Needed

| Approximate Volume of Eluent (ml) | Volume/length Ratio of Dialysis Tubing | Approximate Length Needed for Eluent Sample (cm) | Head Space of 20% (cm) | Approximate Length Needed for Sample plus Headspace (cm) | Approximate Length Needed for Tie Off of Tubing (cm) | Approximate Total Length of Dialysis Tubing Needed (cm) |
|---|---|---|---|---|---|---|
| 39.6 | 2 | 20 | 4 | 24 | 15 | 63 |
| 36.3 | 2 | 18 | 4 | 22 | 15 | 59 |
| 33.0 | 2 | 17 | 3 | 20 | 15 | 55 |
| 29.7 | 2 | 15 | 3 | 18 | 15 | 51 |
| 26.4 | 2 | 13 | 3 | 16 | 15 | 47 |
| 23.1 | 2 | 12 | 2 | 14 | 15 | 43 |
| 19.8 | 2 | 10 | 2 | 12 | 15 | 39 |
| 14.85 | 2 | 7 | 1 | 9 | 15 | 33 |
| 11.55 | 2 | 6 | 1 | 7 | 15 | 29 |
| 6.6 | 2 | 3 | 1 | 4 | 15 | 23 |

Rinse the dialysis tubing thoroughly in DI-H$_2$O. Tie two end knots approximately 7 cm from one end of the dialysis tubing and secure tightly.

Add approximately 5 ml of DI-H$_2$O into the dialysis tubing.

Fill the dialysis tubing with the eluted antibody from the "Eluted Antibody" collection tube.

Tie two end knots approximately 7 cm from the remaining open end of the dialysis tubing and secure tightly. Ensure that the headspace is approximately that as derived from Table 4.

Place the filled and closed dialysis tubing into the dialysis reservoir with the appropriate volume of 1×PBS (from Table 5).

Cover the beaker with clean plastic wrap. Adjust the speed on the stir plate such that the dialysis sample spins freely, but is not pulled down into the vortex of the dialysate. Dialysis should take place at 2° C. to 10° C. with 3 buffer exchanges in total within a 24 hour period.

Antibody Filtration

Label a sterile collection tube "Dialyzed Antibody."

Remove the dialyzed sample tubing from the dialysis beaker. Cut the dialysis tubing open at one end and transfer the dialyzed sample into the "Dialyzed Antibody" centrifuge tube.

Label another sterile collection tube "Dialyzed Antibody."

Select a sterile Luer Lok syringe with adequate capacity to hold the final dialyzed volume.

Attach an Acrodisc® Syringe Filter to the opening of the syringe (0.2 μm HT Tuffryn® Membrane, Low Protein binding, Gelman Laboratories, Cat. No. 4192). Remove the plunger from the syringe and while holding the syringe upright, transfer the dialyzed monoclonal antibody from the "Dialyzed Antibody" tube into the syringe. Replace the plunger.

Hold the Acrodisc® Syringe Filter over the opened, sterile, labeled "Purified Antibody" collection tube, and depress the syringe plunger to filter the purified antibody into the "Purified Antibody" tube.

When filtration is complete, cap the "Purified Antibody" tube and store at 2° C. to 10° C.

Determine concentration of purified monoclonal antibody using A280 procedure.

Example 3

General Method for Epitope Mapping

General Approach

The epitope mapping procedure for the anti-HE4 antibodies, designated 363A90.1 and 363A71.1, are described below. Epitope mapping is typically performed to identify the linear amino acid sequence within an antigenic protein that is recognized by a particular monoclonal antibody (i.e., the epitope). A general approach for epitope mapping requires the expression of the full-length protein, as well as various fragments (i.e., truncated forms) of the protein, generally in a heterologous expression system. These various recombinant proteins are then used to determine if the specific monoclonal antibody is capable of binding to one or more of the truncated forms of the target protein. Through the use of reiterative truncation and the generation of recombinant proteins with overlapping amino acid regions, it is possible to identify the region that is recognized by the monoclonal antibody under investigation. Western blot analysis or ELISA is employed to determine if the specific monoclonal antibody under investigation is capable of binding one or more of the recombinant protein fragments. This approach can ultimately identify the peptide regions that contains the epitope and, in some cases, to refine the epitope precisely to an 8-11 amino acid sequence.

General Epitope Mapping Procedure

Template Generation

The gene of interest is frequently divided into six equal parts. Linear expression truncated fragments are generated using an initial PCR step with the full length gene of interest (e.g., HE4) as a template. The use of overlapping truncations ensures linear epitopes are not missed by being "cut" at fragment junctions.

Second PCR: Addition of Regulatory Elements and GFP (Megapriming)

The full-length gene of interest or gene truncations are then joined with the green fluorescent protein (GFP) using mega-priming. Mega-priming PCR refers to the joining of large DNA fragments with small complementary regions at their ends using PCR. The large DNA fragment that results from the joining of the two or more fragments is then amplified using standard PCR. GFP is used as a fusion partner to ensure robust and stable expression of any particular gene fragment in a Rapid Translation System (RTS). GFP also permits the detection of protein expression levels using anti-GFP antibodies.

The fragments used in mega-priming include the RBS-GFP upstream fragment (765 bp) and the terminator fragment (114 bp). These fragments were isolated from the pSCREEN-GFP plasmid using XbaI/BamHI and XhoI/BspeI digestions, respectively. The RBS-GFP upstream fragment used in mega-priming did not contain the T7 promoter sequence in order to ensure that only full-length PCR products containing both GFP and the gene of interest exhibit stable expression in the RTS reaction. The full-length fragment is finally amplified via short external primers containing the T7 promoter sequence in the sense primer and the T7 terminator sequence in the anti-sense primer. Mega-priming is more suitable for initial PCR sizes less than 1,000 bp. Larger fragments do not give clear single PCR fragments in the second PCR mega-priming reaction. Once the epitope has been identified in a smaller region of the gene, however, the second and third rounds of epitope mapping can be performed using mega-priming.

Protein Expression Using the Rapid Translation of PCR Templates

The GFP-gene fusions created as described above are then used as a template for protein production in the RTS reaction using the RTS 100 *E. coli* HY kit from Roche. The Roche Rapid Translation System (RTS) is a technique that allows the cell-free (in vitro) creation of protein from linear or plasmid DNA sequences under the control of the T7 transcription elements. This process circumvents the time-consuming steps of cloning, cell growth, and cell-lysis steps in *E. coli* cultures for protein production. This reduces the protein expression time approximately 5-fold (i.e., from about 10 days to about 2 days).

Western Blotting and Epitope Mapping

The RTS products are acetone precipitated and loaded directly onto a denaturing polyacrylamide gel and then subjected to western blotting, as detailed below. SDS-PAGE was performed according to the method of Laemmli. All samples were reduced with 20 mM DTT in 1× Nupage LDS sample buffer (Invitrogen) and heated at 70° C. for 10 minutes. Cell lysate was loaded onto a 4-12% Bis-Tris (MES) gel (Invitrogen).

After separation, the proteins were transferred onto a nitrocellulose membrane (Invitrogen) according to the manufacturer's guidelines. After appropriate blocking of the membrane to prevent non-specific binding, the membrane was probed with mouse antibody for 1 hour, followed by incubation with a goat anti-mouse-alkaline phosphatase antibody for 1 hour. The western blot was then visualized with western blue (Promega).

A positive band on a western blot indicates that the epitope is present in that region of the protein. The above steps will narrow the epitope down to one sixth of the original protein of interest. In order to further narrow the epitope down to an 8-12 amino acid region, it is necessary to repeat the above steps, utilizing the region identified as "positive" by western blotting as the starting point for additional rounds of epitope mapping.

Additional Epitope Protocols

If the RTS system does not produce adequate levels of protein for detection by western blot the gene truncations can be cloned directly into the pSCREEN-GFP vector. In this method, the plasmids are transformed into E. coli and induced in log phase using IPTG. Cell pellets are denatured and analyzed as above.

If an antibody fails to recognize a denatured protein bound to nitrocellulose membrane, other methods for detecting an antibody/antigen interaction can be used, including but not limited to ELISA or immunoprecipitation.

Example 4

Characterization of Epitopes for HE4 Monoclonal Antibodies 363A90.1 and 363A71.1

Epitope mapping for HE4 monoclonal antibodies 363A90.1 and 363A71.1 was carried out essentially as described in Example 3. Specifically, PCR was used to create HE4 gene truncations, followed by RTS to generate recombinant HE4 protein fragments, and finally western blotting to detect antibody binding to HE4 protein fragments. GFP was joined with the HE4 gene truncations in a second round of PCR to ensure robust and stable expression in RTS.

The full-length amino acid sequence for HE4-T1 (i.e., isoform 1; SEQ ID NO:1) has a size of 124 amino acid residues. The following sequential steps were carried out in order to epitope map the HE4-363A90.1 antibody:

The HE4 protein was equally divided into six regions [1-6] of approximately twenty amino acids each. Overlapping sequences, which contain homologous sequence to permit mega priming during a second PCR cycle and restriction sites for a second option of sub-cloning into pScreen-GFP plasmid, were added to the HE4 gene during the first PCR. The first round of PCR created fragments of the HE4 protein (SEQ ID NO:1) including: region [1] (i.e., amino acids 1-20); region [1-2] (i.e., amino acids 1-40); region [1-3] (i.e., amino acids 1-60); region [1-4] (i.e., amino acids 1-80); region [1-5] (i.e., amino acids 1-102); region [1-6] (i.e., amino acids 1-124); and finally region [2-6] (i.e., amino acids 21-124). Individual regions (e.g., region [5] alone) were not expressed to avoid missing epitopes that were present in junction sequence between regions.

The first round PCR products of HE4 were produced as described above and were subcloned into pSCREEN-GFP (BamH1-XhoI). The GFP-gene fusions created were used as a template for protein production in the RTS reaction using the RTS 100 E. coli HY kit from Roche. The protein products from RTS were acetone precipitated, loaded directly onto a denaturing polyacrylamide gel, and analyzed by western blotting. The western blot was probed directly with the 363A90.1 monoclonal antibody and GFP antibodies. A positive band was detected in region [5]. The above process was repeated using a fragment comprising the last five amino acids of region [4] and full-length region [5] as the starting sequence.

A second round of RTS produced a positive result for the 363A90.1 antibody in the region designated 5Q3 (VNINFPQLGLCR (SEQ ID NO:11)); corresponding to amino acid residues 83-94 of SEQ ID NO:1).

Results

Initial results showed that the epitope for the HE4 monoclonal antibody 363A90.1 is located within the C-terminal region of the HE4 protein. An additional truncation of the HE4 protein showed that the epitope recognized by 363A90.1 is (VNINFPQLGLCR (SEQ ID NO:11); corresponding to amino acid residues 83 to 94 of SEQ ID NO:1).

The identical process described above was used to identify the epitope for HE4 monoclonal antibody 363A71.1. Initial results indicated that the epitope was located within the C-terminal region of the HE4 protein. The epitope was preliminarily defined to a twenty-four amino acid region, specifically corresponding to amino acid residues 93 to 116 of SEQ ID NO:1 (CRDQCQVDSQCPGQMKCCRNGCGK (SEQ ID NO:12)). The refined epitope likely lies in the twenty amino acid region consisting of CRDQCQVDSQCPGQMKCCRN (SEQ ID NO:13; corresponding to amino acid residues 93 to 112 of SEQ ID NO:1). Notably, the identified epitopes for 363A90.1 and 363A71.1 are present in the T1, T4, and T5 isoforms of HE4.

Example 5

Detection of HE4 Overexpression in Normal and Ovarian Cancer Serum Samples Using a Sandwich ELISA Format The utility of the monoclonal HE4 antibodies of the present invention, specifically 363A90.1 and 363A71.1, to detect early stage ovarian cancer was investigated. The composition of the patient sample cohort is set forth in Table 7 below:

TABLE 7

Ovarian Cancer Study Cohort

| Sample Description/Diagnosis | Number of Samples |
| --- | --- |
| Stage 1 ovarian cancer | 67 |
| Stage 2 ovarian cancer | 66 |
| Stage 3 ovarian cancer | 67 |
| Normal (non-cancerous) | 396 |

All of the samples were analyzed using the 363A90.1 and 363A71.1 antibodies of the invention in a sandwich ELISA format, in accordance with the methods described herein. Specifically, the methods were performed as described below:

Coating of Assay Plates:

96-well plates were coated with 100 µl/well of the primary antibody (i.e., anti-HE4 monoclonal antibody 363A90.1) at 2 µg/ml in PBS, and the plates were incubated at 4° C. overnight. The next day the plates were washed five times with PBS and then 250 µl/well of PBS/3% BSA was added to each well and the plates were incubated for 2 hours at 30° C. The plates were then emptied and dried in a vacuum oven for 2 hours at room temperature. The plates were heat-sealed inside a mylar foil bag along with a desiccant pack and stored at 4° C. prior to use.

Sandwich ELISA Method:

The foil bags containing the assay plates were warmed to room temperature immediately prior to use in the assay. The serum samples were diluted 1:4 into PBS/1% Bovine Serum/ 0.05% Tween® 20/1 mg/ml mouse IgG. The HE4 antigen protein standard was diluted to 100 ng/ml, then serially diluted two-fold into PBS/1% Bovine Serum/0.05% Tween 20®/1 mg/ml mouse IgG. All of the individual standard curve samples were further diluted 1:4 into the buffer so that they would be diluted to the same extent as the serum samples. 100 µl/well of the diluted serum samples and the standard curve samples were added to the anti-HE4 coated assay plates. The plates were incubated for 2 hours at 30° C. and then washed five times with PBS-0.05% Tween® 20 (250 µl/well).

The secondary (or tag) antibody (i.e., anti-HE4 monoclonal 363A71.1 coupled to HRP), was diluted 1:16,000 into PBS/1% bovine IgG/0.05% Tween® 20/1 mg/ml mouse IgG. 100 µl/well of the secondary antibody solution was added to the aspirated plates and incubated for 1 hour at 30° C. The plates were then washed five times with PBS-0.05% Tween® 20 (250 µl/well). The developing solution used to detect antigen-antibody binding, TMB(3,3',5,5'-Tetramethylbenzidine) was warmed to room temperature prior to use, and then the TMB was added to the aspirated plates at 100 µl/well. The plates were incubated for 10 minutes at room temperature and then the stop solution (i.e., 2N H2SO4) was added to the plates containing the TMB at 100 µl/well.

The plates were then incubated for 10 minutes at room temperature and read on the Molecular Devices SpectraMax plate reader at 450 nm, with a reference wavelength of 650 nm, using SoftMax Pro software. The data were saved as SoftMax Pro files and also exported as Text files for use with MS Excel.

The controls for the sandwich ELISA assay included Uniglobe # 72372 (serum used as the high control), Uniglobe # 72404 (serum used as the low control), and PBS/1% Bovine Serum/0.05% Tween® 20/1 mg/ml mouse IgG (buffer control).

Classification of Samples as "Positive" or "Negative" and Assay Results

A cutoff threshold of two times the standard deviation was obtained from a second independent patient sample cohort from 104-normal, postmenopausal women and used to classify a result as "positive" or "negative." The results of these studies are presented in Table 8:

TABLE 8

Detection of HE4 Overexpression as a Diagnostic Tool for Ovarian Cancer

| Sample Description/Diagnosis | Number of Samples | Sensitivity |
|---|---|---|
| Stage 1 ovarian cancer | 67 | 63% (42 positives of 67 total) |
| Stage 2 ovarian cancer | 66 | 62% (41 positives of 66 total) |
| Stage 3 ovarian cancer | 67 | 74% (50 positives of 67 total) |

Example 6

Detection of HE4 Overexpression in Breast Cancer Sera Samples

The ability of HE4 overexpression to detect breast cancer in serum samples from twenty-seven breast cancer patients of various ages (i.e., age 53 to 97) was assessed.

All of the samples were analyzed using in the "sandwich" ELISA format, essentially as described above in Example 5. A cutoff threshold of two times the standard deviation was obtained from a second independent cohort of normal, non-cancerous samples and used to classify a result as "positive" or "negative." The results of these studies are presented in Table 10:

TABLE 10

Detection of HE4 Overexpression as a Diagnostic Tool for Breast Cancer

| Sample Description/Diagnosis | Number of Samples | Sensitivity |
|---|---|---|
| Breast Cancer | 27 | 59% (16 positives of 27 total) |

Figure 1B:
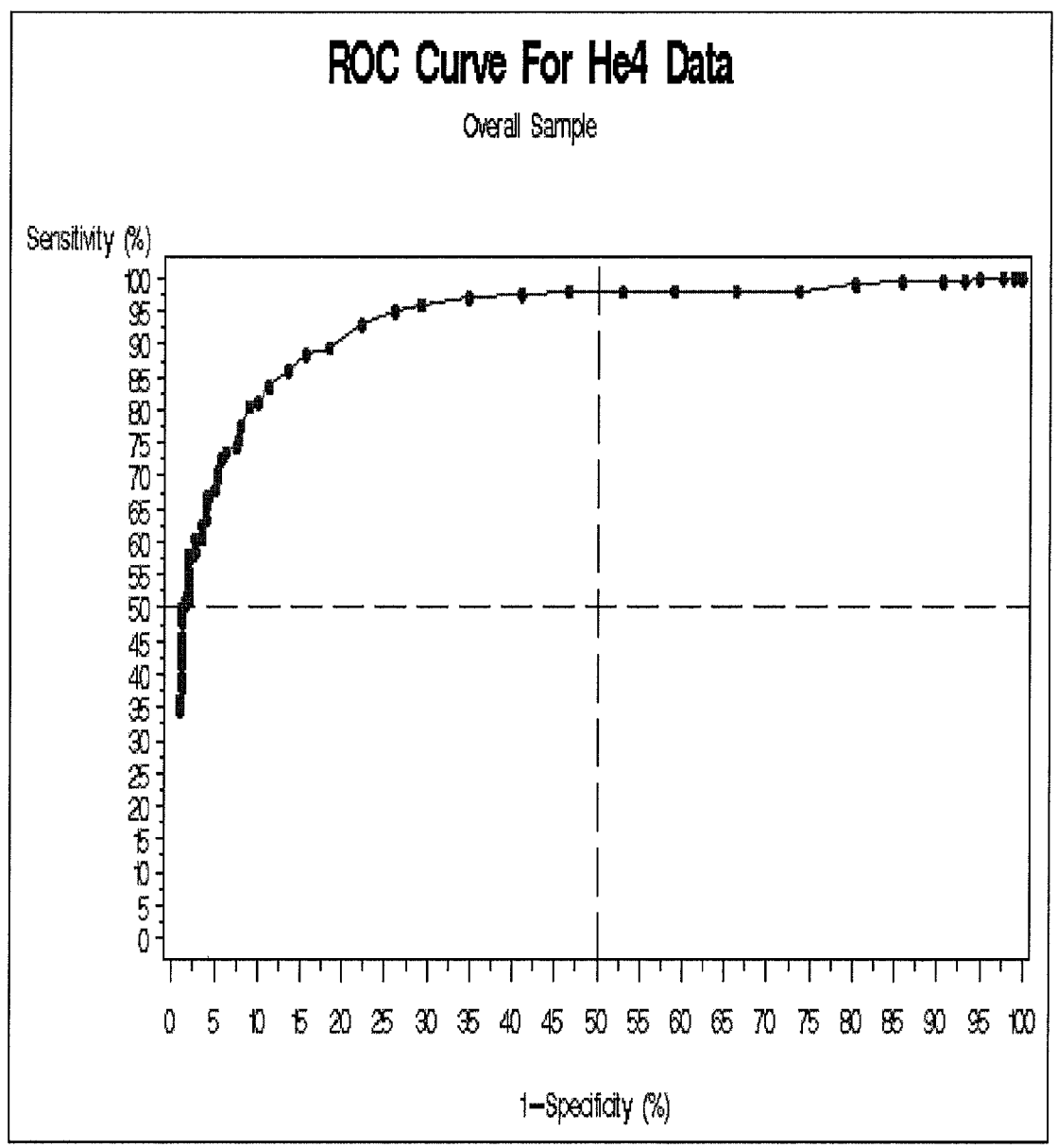

Receiver Operating Characteristic (ROC) plots for HE4 obtained with samples from patients over the age of 55 and with patient samples of various ages using the HE4 monoclonal antibodies designated as 363A90.1 and 363A71.1 are presented in FIG. 1.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A monoclonal antibody that is capable of specifically binding to HE4, wherein the antibody is selected from the group consisting of:
   (a) the monoclonal antibody produced by the hybridoma cell line 363A90.1, deposited with the ATCC as Patent Deposit No. PTA-8196;
   (b) a monoclonal antibody that binds to the amino acid sequence set forth in SEQ ID NO:11; and,
   (c) a monoclonal antibody that is an antigen binding fragment of a monoclonal antibody of (a) or (b), wherein the fragment retains the capability of specifically binding to HE4.

2. The hybridoma cell line 363A90.1, deposited with the ATCC as Patent Deposit No. PTA-8196.

3. The hybridoma cell line 363A71.1, deposited with the ATCC as Patent Deposit No. PTA-8195.

4. A hybridoma cell line capable of producing a monoclonal antibody of claim 1.

5. A kit for diagnosing ovarian cancer in a patient comprising:
   a) a capture antibody immobilized on a solid support, wherein the capture antibody is a first HE4 antibody; and
   b) a tag antibody, wherein the tag antibody is a second HE4 antibody that is labeled with a detectable substance;
   wherein said first or said second HE4 antibody is the monoclonal antibody of claim 1.

6. The kit of claim 5, wherein the capture antibody is the monoclonal antibody produced by the hybridoma cell line 363A90.1, deposited with the ATCC as Patent Deposit No. PTA-8196, and wherein the tag antibody is the monoclonal antibody produced by the hybridoma cell line 363A71.1, deposited with the ATCC as Patent Deposit No. PTA-8195.

7. A kit for diagnosing ovarian cancer comprising at least one monoclonal antibody according to claim 1.

8. The kit of claim 7, wherein the monoclonal antibody is the monoclonal antibody produced by the hybridoma cell line 363A90.1, deposited with the ATCC as Patent Deposit No. PTA-8196.

9. The kit of claim 7 comprising at least two antibodies, wherein a first antibody is the monoclonal antibody produced by the hybridoma cell line 363A90.1, deposited with the ATCC as Patent Deposit No. PTA-8196, and a second antibody is the monoclonal antibody produced by the hybridoma cell line 363A71.1, deposited with the ATCC as Patent Deposit No. PTA-8195.

10. A method for producing an HE4 antibody comprising immunizing an animal with a polypeptide consisting of the amino acid sequence set forth in SEQ ID NO:11.

11. A method for producing an HE4 monoclonal antibody comprising:
    (a) immunizing an animal with a polypeptide under conditions to elicit an immune response, wherein said polypeptide consists of the amino acid sequence set forth in SEQ ID NO:11;
    (b) isolating antibody-producing cells from the animal;
    (c) fusing the antibody-producing cells with immortalized cells in culture to form monoclonal antibody-producing hybridoma cells;
    (d) culturing the hybridoma cells; and,
    (e) isolating monoclonal antibodies from culture.

* * * * *

SEQUENCE LISTING

<160> NUMBER OF SEQ ID NOS: 16

<210> SEQ ID NO 1
<211> LENGTH: 124
<212> TYPE: PRT
<213> ORGANISM: Homo sapiens
<220> FEATURE:
<221> NAME/KEY: PEPTIDE -continued

```
<222> LOCATION: (1)...(124)
<223> OTHER INFORMATION: HE4 isoform 1

<400> SEQUENCE: 1

Met Pro Ala Cys Arg Leu Gly Pro Leu Ala Ala Leu Leu Leu Ser
 1               5                  10                  15

Leu Leu Leu Phe Gly Phe Thr Leu Val Ser Gly Thr Gly Ala Glu Lys
                20                  25                  30

Thr Gly Val Cys Pro Glu Leu Gln Ala Asp Gln Asn Cys Thr Gln Glu
            35                  40                  45

Cys Val Ser Asp Ser Glu Cys Ala Asp Asn Leu Lys Cys Cys Ser Ala
50                  55                  60

Gly Cys Ala Thr Phe Cys Ser Leu Pro Asn Asp Lys Glu Gly Ser Cys
65                  70                  75                  80

Pro Gln Val Asn Ile Asn Phe Pro Gln Leu Gly Leu Cys Arg Asp Gln
                85                  90                  95

Cys Gln Val Asp Ser Gln Cys Pro Gly Gln Met Lys Cys Cys Arg Asn
                100                 105                 110

Gly Cys Gly Lys Val Ser Cys Val Thr Pro Asn Phe
            115                 120

<210> SEQ ID NO 2
<211> LENGTH: 570
<212> TYPE: DNA
<213> ORGANISM: Homo sapiens
<220> FEATURE:
<221> NAME/KEY: CDS
<222> LOCATION: (29)...(403)

<400> SEQUENCE: 2
cacctgcacc ccgcccgggc atagcacc atg cct gct tgt cgc cta ggc ccg      52
                                Met Pro Ala Cys Arg Leu Gly Pro
                                 1               5 cta gcc gcc gcc ctc ctc ctc agc ctg ctg ctg ttc ggc ttc acc cta    100
Leu Ala Ala Ala Leu Leu Leu Ser Leu Leu Leu Phe Gly Phe Thr Leu
    10                  15                  20 gtc tca ggc aca gga gca gag aag act ggc gtg tgc ccc gag ctc cag    148
Val Ser Gly Thr Gly Ala Glu Lys Thr Gly Val Cys Pro Glu Leu Gln
25                  30                  35                  40 gct gac cag aac tgc acg caa gag tgc gtc tcg gac agc gaa tgc gcc    196
Ala Asp Gln Asn Cys Thr Gln Glu Cys Val Ser Asp Ser Glu Cys Ala
                45                  50                  55 gac aac ctc aag tgc tgc agc gcg ggc tgt gcc acc ttc tgc tct ctg    244
Asp Asn Leu Lys Cys Cys Ser Ala Gly Cys Ala Thr Phe Cys Ser Leu
                60                  65                  70 ccc aat gat aag gag ggt tcc tgc ccc cag gtg aac att aac ttt ccc    292
Pro Asn Asp Lys Glu Gly Ser Cys Pro Gln Val Asn Ile Asn Phe Pro
            75                  80                  85 cag ctc ggc ctc tgt cgg gac cag tgc cag gtg gac agc cag tgt cct    340
Gln Leu Gly Leu Cys Arg Asp Gln Cys Gln Val Asp Ser Gln Cys Pro
    90                  95                  100 ggc cag atg aaa tgc tgc cgc aat ggc tgt ggg aag gtg tcc tgt gtc    388
Gly Gln Met Lys Cys Cys Arg Asn Gly Cys Gly Lys Val Ser Cys Val
105                 110                 115                 120 act ccc aat ttc tga gctccagcca ccaccaggct gagcagtgag gagagaaagt    443
Thr Pro Asn Phe * ttctgcctgg ccctgcatct ggttccagcc cacctgccct ccccttttc gggactctgt    503 attccctctt gggctgacca cagcttctcc ctttcccaac caataaagta accactttca    563
```

-continued

```
gcaaaaa                                                                      570

<210> SEQ ID NO 3
<211> LENGTH: 102
<212> TYPE: PRT
<213> ORGANISM: Homo sapiens
<220> FEATURE:
<221> NAME/KEY: PEPTIDE
<222> LOCATION: (1)...(102)
<223> OTHER INFORMATION: HE4 isoform 2

<400> SEQUENCE: 3

Met Pro Ala Cys Arg Leu Gly Pro Leu Ala Ala Leu Leu Leu Ser
 1               5                  10                  15

Leu Leu Leu Phe Gly Phe Thr Leu Val Ser Gly Thr Gly Ala Glu Lys
             20                  25                  30

Thr Gly Val Cys Pro Glu Leu Gln Ala Asp Gln Asn Cys Thr Gln Glu
         35                  40                  45

Cys Val Ser Asp Ser Glu Cys Ala Asp Asn Leu Lys Cys Cys Ser Ala
     50                  55                  60

Gly Cys Ala Thr Phe Cys Ser Leu Pro Asn Ala Leu Phe His Trp His
 65                  70                  75                  80

Leu Lys Thr Arg Arg Leu Trp Glu Ile Ser Gly Pro Arg Pro Arg Arg
                 85                  90                  95

Pro Thr Trp Asp Ser Ser
            100

<210> SEQ ID NO 4
<211> LENGTH: 358
<212> TYPE: DNA
<213> ORGANISM: Homo sapiens
<220> FEATURE:
<221> NAME/KEY: CDS
<222> LOCATION: (29)...(337)

<400> SEQUENCE: 4
cacctgcacc ccgcccgggc atagcacc atg cct gct tgt cgc cta ggc ccg         52
                              Met Pro Ala Cys Arg Leu Gly Pro
                                1               5 cta gcc gcc gcc ctc ctc ctc agc ctg ctg ctg ttc ggc ttc acc cta       100
Leu Ala Ala Ala Leu Leu Leu Ser Leu Leu Leu Phe Gly Phe Thr Leu
     10                  15                  20 gtc tca ggc aca gga gca gag aag act ggc gtg tgc ccc gag ctc cag       148
Val Ser Gly Thr Gly Ala Glu Lys Thr Gly Val Cys Pro Glu Leu Gln
 25                  30                  35                  40 gct gac cag aac tgc acg caa gag tgc gtc tcg gac agc gaa tgc gcc       196
Ala Asp Gln Asn Cys Thr Gln Glu Cys Val Ser Asp Ser Glu Cys Ala
                 45                  50                  55 gac aac ctc aag tgc tgc agc gcg ggc tgt gcc acc ttc tgc tct ctg       244
Asp Asn Leu Lys Cys Cys Ser Ala Gly Cys Ala Thr Phe Cys Ser Leu
             60                  65                  70 ccc aat gca ctg ttc cac tgg cac cta aag aca cgg agg ctc tgg gag       292
Pro Asn Ala Leu Phe His Trp His Leu Lys Thr Arg Arg Leu Trp Glu
         75                  80                  85 att tct ggc cct agg cca cga agg ccc act tgg gac tca agc tga           337
Ile Ser Gly Pro Arg Pro Arg Arg Pro Thr Trp Asp Ser Ser     *
     90                  95                 100 ggtcctgtga ttccatttgg g                                                358

<210> SEQ ID NO 5
<211> LENGTH: 79
```

```
<212> TYPE: PRT
<213> ORGANISM: Homo sapiens
<220> FEATURE:
<221> NAME/KEY: PEPTIDE
<222> LOCATION: (1)...(79)
<223> OTHER INFORMATION: HE4 isoform 3

<400> SEQUENCE: 5

Met Pro Ala Cys Arg Leu Gly Pro Leu Ala Ala Ala Leu Leu Leu Ser
 1               5                  10                  15

Leu Leu Leu Phe Gly Phe Thr Leu Val Ser Gly Thr Gly Ala Glu Lys
             20                  25                  30

Thr Gly Val Cys Pro Glu Leu Gln Ala Asp Gln Asn Cys Thr Gln Glu
         35                  40                  45

Cys Val Ser Asp Ser Glu Cys Ala Asp Asn Leu Lys Cys Cys Ser Ala
 50                  55                  60

Gly Cys Ala Thr Phe Cys Ser Leu Pro Asn Gly Gln Leu Ala Glu
 65                  70                  75

<210> SEQ ID NO 6
<211> LENGTH: 694
<212> TYPE: DNA
<213> ORGANISM: Homo sapiens
<220> FEATURE:
<221> NAME/KEY: CDS
<222> LOCATION: (29)...(268)

<400> SEQUENCE: 6
cacctgcacc ccgcccgggc atagcacc atg cct gct tgt cgc cta ggc ccg       52
                                Met Pro Ala Cys Arg Leu Gly Pro
                                 1               5 cta gcc gcc gcc ctc ctc ctc agc ctg ctg ctg ttc ggc ttc acc cta    100
Leu Ala Ala Ala Leu Leu Leu Ser Leu Leu Leu Phe Gly Phe Thr Leu
        10                  15                  20 gtc tca ggc aca gga gca gag aag act ggc gtg tgc ccc gag ctc cag    148
Val Ser Gly Thr Gly Ala Glu Lys Thr Gly Val Cys Pro Glu Leu Gln
 25                  30                  35                  40 gct gac cag aac tgc acg caa gag tgc gtc tcg gac agc gaa tgc gcc    196
Ala Asp Gln Asn Cys Thr Gln Glu Cys Val Ser Asp Ser Glu Cys Ala
                 45                  50                  55 gac aac ctc aag tgc tgc agc gcg ggt tgt gcc acc ttc tgc tct ctg    244
Asp Asn Leu Lys Cys Cys Ser Ala Gly Cys Ala Thr Phe Cys Ser Leu
             60                  65                  70 ccc aat ggc caa ctg gct gag tga ttcgaagaaa gtgaggaatc ctccctggac   298
Pro Asn Gly Gln Leu Ala Glu  *
         75 actgtatcgc ccttcgtcgt ctttcagtca atctcttcca ctctaaggat tgagtgagcg   358 cgagctgggg actctctcaa agataaggag ggttcctgcc cccaggtgaa cattaacttt   418 ccccagctcg gcctctgtcg ggaccagtgc caggtggaca gccagtgtcc tggccagatg   478 aaatgctgcc gcaatggctg tgggaaggtg tcctgtgtca ctcccaattt ctgaggtcca   538 gccaccacca ggctgagcag tgaggagaga aagtttctgc ctggccctgc atctggttcc   598 agcccacctg ccctcccctt tttcgggact ctgtattccc tcttgggctg accacagctt   658 ctcccttttcc caaccaataa agtaaccact ttcagc                            694

<210> SEQ ID NO 7
<211> LENGTH: 76
<212> TYPE: PRT
<213> ORGANISM: Homo sapiens
<220> FEATURE:
```

```
<221> NAME/KEY: PEPTIDE
<222> LOCATION: (1)...(76)
<223> OTHER INFORMATION: HE4 isoform 4

<400> SEQUENCE: 7

Met Pro Ala Cys Arg Leu Gly Pro Leu Ala Ala Ala Leu Leu Leu Ser
1               5                   10                  15

Leu Leu Leu Phe Gly Phe Thr Leu Val Ser Asp Lys Glu Gly Ser Cys
            20                  25                  30

Pro Gln Val Asn Ile Asn Phe Pro Gln Leu Gly Leu Cys Arg Asp Gln
        35                  40                  45

Cys Gln Val Asp Ser Gln Cys Pro Gly Gln Met Lys Cys Cys Arg Asn
    50                  55                  60

Gly Cys Gly Lys Val Ser Cys Val Thr Pro Asn Phe
65                  70                  75

<210> SEQ ID NO 8
<211> LENGTH: 421
<212> TYPE: DNA
<213> ORGANISM: Homo sapiens
<220> FEATURE:
<221> NAME/KEY: CDS
<222> LOCATION: (29)...(259)

<400> SEQUENCE: 8
cacctgcacc ccgcccgggc atagcacc atg cct gct tgt cgc cta ggc ccg        52
                              Met Pro Ala Cys Arg Leu Gly Pro
                               1               5 cta gcc gcc gcc ctc ctc ctc agc ctg ctg ctg ttc ggc ttc acc cta      100
Leu Ala Ala Ala Leu Leu Leu Ser Leu Leu Leu Phe Gly Phe Thr Leu
        10                  15                  20 gtc tca gat aag gag ggt tcc tgc ccc cag gtg aac att aac ttt ccc      148
Val Ser Asp Lys Glu Gly Ser Cys Pro Gln Val Asn Ile Asn Phe Pro
 25                  30                  35                  40 cag ctc ggc ctc tgt cgg gac cag tgc cag gtg gac agc cag tgt cct      196
Gln Leu Gly Leu Cys Arg Asp Gln Cys Gln Val Asp Ser Gln Cys Pro
                45                  50                  55 ggc cag atg aaa tgc tgc cgc aat ggc tgt ggg aag gtg tcc tgt gtc      244
Gly Gln Met Lys Cys Cys Arg Asn Gly Cys Gly Lys Val Ser Cys Val
            60                  65                  70 act ccc aat ttc tga ggtccagcca ccaccaggct gagcagtgag gagagaaagt      299
Thr Pro Asn Phe *
        75 ttctgcctgg ccctgcatct ggttccagcc cacctgccct ccccttttc gggactctgt     359 attccctctt gggctgacca cagcttctcc ctttcccaac caataaagta accactttca    419 gc                                                                    421

<210> SEQ ID NO 9
<211> LENGTH: 73
<212> TYPE: PRT
<213> ORGANISM: Homo sapiens
<220> FEATURE:
<221> NAME/KEY: PEPTIDE
<222> LOCATION: (1)...(73)
<223> OTHER INFORMATION: HE4 isoform 5

<400> SEQUENCE: 9

Met Leu Gln Val Gln Val Asn Leu Pro Val Ser Pro Leu Pro Thr Tyr
1               5                   10                  15

Pro Tyr Ser Phe Phe Tyr Pro Asp Lys Glu Gly Ser Cys Pro Gln Val
            20                  25                  30
```

```
Asn Ile Asn Phe Pro Gln Leu Gly Leu Cys Arg Asp Gln Cys Gln Val
        35                  40                  45

Asp Ser Gln Cys Pro Gly Gln Met Lys Cys Cys Arg Asn Gly Cys Gly
    50                  55                  60

Lys Val Ser Cys Val Thr Pro Asn Phe
65                  70

<210> SEQ ID NO 10
<211> LENGTH: 411
<212> TYPE: DNA
<213> ORGANISM: Homo sapiens
<220> FEATURE:
<221> NAME/KEY: CDS
<222> LOCATION: (28)...(249)

<400> SEQUENCE: 10
agcccagtga ggggcagtgg gggggcc atg ctg cag gta caa gtt aat ctc cct        54
                            Met Leu Gln Val Gln Val Asn Leu Pro
                              1               5 gta tcg cct ctg ccc act tac cct tac tcc ttt ttc tac cca gat aag        102
Val Ser Pro Leu Pro Thr Tyr Pro Tyr Ser Phe Phe Tyr Pro Asp Lys
 10                  15                  20                  25 gag ggt tcc tgc ccc cag gtg aac att aac ttt ccc cag ctc ggc ctc        150
Glu Gly Ser Cys Pro Gln Val Asn Ile Asn Phe Pro Gln Leu Gly Leu
                 30                  35                  40 tgt cgg gac cag tgc cag gtg gac agc cag tgt cct ggc cag atg aaa        198
Cys Arg Asp Gln Cys Gln Val Asp Ser Gln Cys Pro Gly Gln Met Lys
             45                  50                  55 tgc tgc cgc aat ggc tgt ggg aag gtg tcc tgt gtc act ccc aat ttc        246
Cys Cys Arg Asn Gly Cys Gly Lys Val Ser Cys Val Thr Pro Asn Phe
         60                  65                  70 tga ggtccagcca ccaccaggct gagcagtgag gagagaaagt ttctgcctgg              299
*
ccctgcatct ggttccagcc cacctgccct cccctttttc gggactctgt attccctctt      359
gggctgacca cagcttctcc ctttcccaac caataaagta accactttca gc              411

<210> SEQ ID NO 11
<211> LENGTH: 12
<212> TYPE: PRT
<213> ORGANISM: Artificial Sequence
<220> FEATURE:
<223> OTHER INFORMATION: Epitope sequence in HE4 for monoclonal antibody
      363A90.1

<400> SEQUENCE: 11

Val Asn Ile Asn Phe Pro Gln Leu Gly Leu Cys Arg
  1               5                  10

<210> SEQ ID NO 12
<211> LENGTH: 24
<212> TYPE: PRT
<213> ORGANISM: Artificial Sequence
<220> FEATURE:
<223> OTHER INFORMATION: Epitope sequence in HE4 for monoclonal antibody
      363A71.1

<400> SEQUENCE: 12

Cys Arg Asp Gln Cys Gln Val Asp Ser Gln Cys Pro Gly Gln Met Lys
  1               5                  10                  15

Cys Cys Arg Asn Gly Cys Gly Lys
             20
```

-continued

```
<210> SEQ ID NO 13
<211> LENGTH: 20
<212> TYPE: PRT
<213> ORGANISM: Artificial Sequence
<220> FEATURE:
<223> OTHER INFORMATION: Epitope sequence in HE4 for monoclonal antibody
      363A71.1 (putative refined epitope sequence)

<400> SEQUENCE: 13

Cys Arg Asp Gln Cys Gln Val Asp Ser Gln Cys Pro Gly Gln Met Lys
1               5                   10                  15

Cys Cys Arg Asn
            20

<210> SEQ ID NO 14
<211> LENGTH: 27
<212> TYPE: PRT
<213> ORGANISM: Artificial Sequence
<220> FEATURE:
<223> OTHER INFORMATION: HE4 fragment comprising five amino acids of
      region 4 and all of region 5
<221> NAME/KEY: PEPTIDE
<222> LOCATION: (1)...(5)
<223> OTHER INFORMATION: Portion of region 4 of HE4
<221> NAME/KEY: PEPTIDE
<222> LOCATION: (6)...(27)
<223> OTHER INFORMATION: Region 5 of HE4

<400> SEQUENCE: 14

Lys Glu Gly Ser Cys Pro Gln Val Asn Ile Asn Phe Pro Gln Leu Gly
1               5                   10                  15

Leu Cys Arg Asp Gln Cys Gln Val Asp Ser Gln
            20                  25

<210> SEQ ID NO 15
<211> LENGTH: 12
<212> TYPE: PRT
<213> ORGANISM: Artificial Sequence
<220> FEATURE:
<223> OTHER INFORMATION: HE4 fragment comprising five amino acids of
      region 4 and seven amino acids of region 5 [fragment 5Q1]
<221> NAME/KEY: PEPTIDE
<222> LOCATION: (1)...(5)
<223> OTHER INFORMATION: Five amino acids of region 4 of HE4
<221> NAME/KEY: PEPTIDE
<222> LOCATION: (6)...(12)
<223> OTHER INFORMATION: Seven amino acids of region 5 of HE4

<400> SEQUENCE: 15

Lys Glu Gly Ser Cys Pro Gln Val Asn Ile Asn Phe
1               5                   10

<210> SEQ ID NO 16
<211> LENGTH: 12
<212> TYPE: PRT
<213> ORGANISM: Artificial Sequence
<220> FEATURE:
<223> OTHER INFORMATION: HE4 fragment comprising twelve amino acids of
      region 5 [fragment 5Q2]
<221> NAME/KEY: PEPTIDE
<222> LOCATION: (1)...(12)
<223> OTHER INFORMATION: Twelve amino acids of region 5 of HE4

<400> SEQUENCE: 16

Gly Leu Cys Arg Asp Gln Cys Gln Val Asp Ser Gln
1               5                   10
```